United States Patent
Imamura et al.

(10) Patent No.: US 12,053,314 B2
(45) Date of Patent: Aug. 6, 2024

(54) MOBILE RADIOGRAPHY APPARATUS

(71) Applicant: FUJIFILM CORPORATION, Tokyo (JP)

(72) Inventors: Ryo Imamura, Kanagawa (JP); Takeyasu Kobayashi, Kanagawa (JP)

(73) Assignee: FUJIFILM CORPORATION, Tokyo. (JP)

( * ) Notice: Subject to any disclaimer, the term of this patent is extended or adjusted under 35 U.S.C. 154(b) by 292 days.

(21) Appl. No.: 17/713,203

(22) Filed: Apr. 4, 2022

(65) Prior Publication Data

US 2022/0330908 A1  Oct. 20, 2022

(30) Foreign Application Priority Data

Apr. 15, 2021 (JP) ................................. 2021-069372

(51) Int. Cl.
| | |
|---|---|
| *A61B 6/40* | (2024.01) |
| *A61B 6/00* | (2006.01) |
| *H01Q 3/06* | (2006.01) |

(52) U.S. Cl.
CPC .......... *A61B 6/4405* (2013.01); *A61B 6/4441* (2013.01); *A61B 6/56* (2013.01); *H01Q 3/06* (2013.01)

(58) Field of Classification Search
CPC ....... A61B 6/4405; A61B 6/4441; A61B 6/56; H01Q 3/06
See application file for complete search history.

(56) References Cited

U.S. PATENT DOCUMENTS

| | | | |
|---|---|---|---|
| 2002/0085682 A1 | 7/2002 | Noegel et al. | |
| 2008/0049901 A1* | 2/2008 | Tamakoshi | A61B 6/467 378/98.2 |
| 2009/0034683 A1 | 2/2009 | Tamakoshi | |

(Continued)

FOREIGN PATENT DOCUMENTS

| | | |
|---|---|---|
| EP | 2380496 A1 | 10/2011 |
| WO | 2006/101231 A1 | 9/2006 |

OTHER PUBLICATIONS

Extended European Search Report dated Sep. 2, 2022, issued in corresponding EP Patent Application No. 22167233.0.

*Primary Examiner* — Hugh Maupin
(74) *Attorney, Agent, or Firm* — SOLARIS Intellectual Property Group, PLLC

(57) ABSTRACT

Provided is a mobile radiography apparatus capable of performing relatively stable wireless communication even in a case in which the mobile radiography apparatus is moved due to traveling of a carriage or an arm is rotated.

A mobile radiography apparatus includes a radiation source, a radiation image detector that detects a radiation image of a subject by receiving radiation emitted from the radiation source and transmitted through the subject, an arm that holds the radiation source and the radiation image detector, a body part to which the arm is rotatably attached, a carriage on which the body part is mounted, and an antenna that emits a radio wave for wirelessly communicating with an external apparatus, the antenna being provided in a portion in which a radiation direction of the radio wave is not changed even in a case in which the arm is rotated and capable of changing the radiation direction of the radio wave.

18 Claims, 24 Drawing Sheets

(56) References Cited

U.S. PATENT DOCUMENTS

| | | | |
|---|---|---|---|
| 2015/0327833 A1* | 11/2015 | Tsuchiya | A61B 6/4405 |
| | | | 378/91 |
| 2017/0140121 A1* | 5/2017 | Schulhauser | G16H 30/20 |
| 2018/0296174 A1* | 10/2018 | Barker | A61B 6/4441 |
| 2020/0158278 A1 | 5/2020 | Daugirdas et al. | |
| 2020/0348395 A1* | 11/2020 | Belot | G01S 7/032 |
| 2022/0240883 A1* | 8/2022 | Kingma | G16H 40/67 |

* cited by examiner

FIG. 2
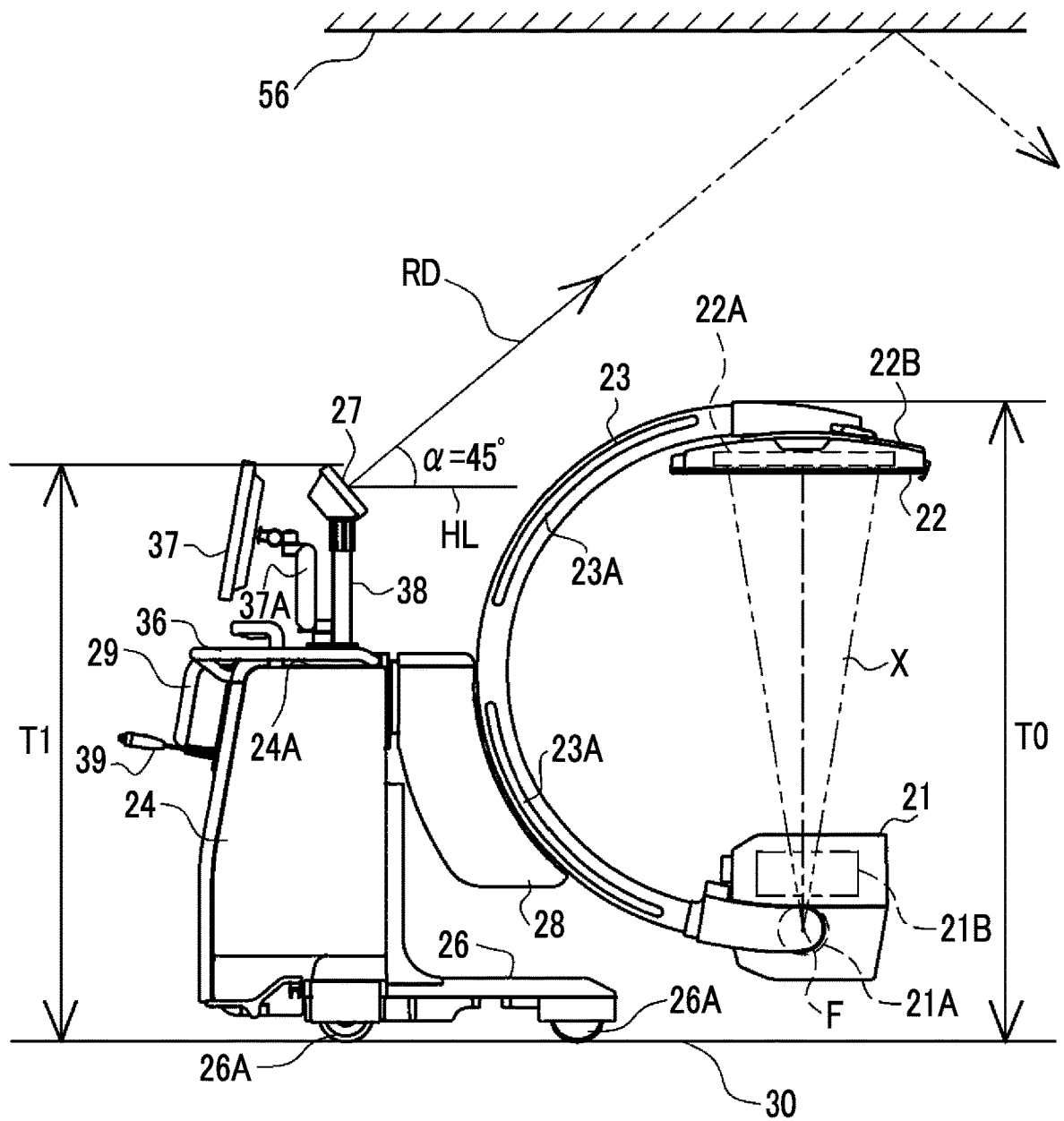
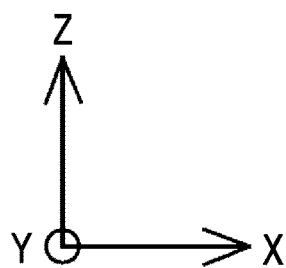

FIG. 8
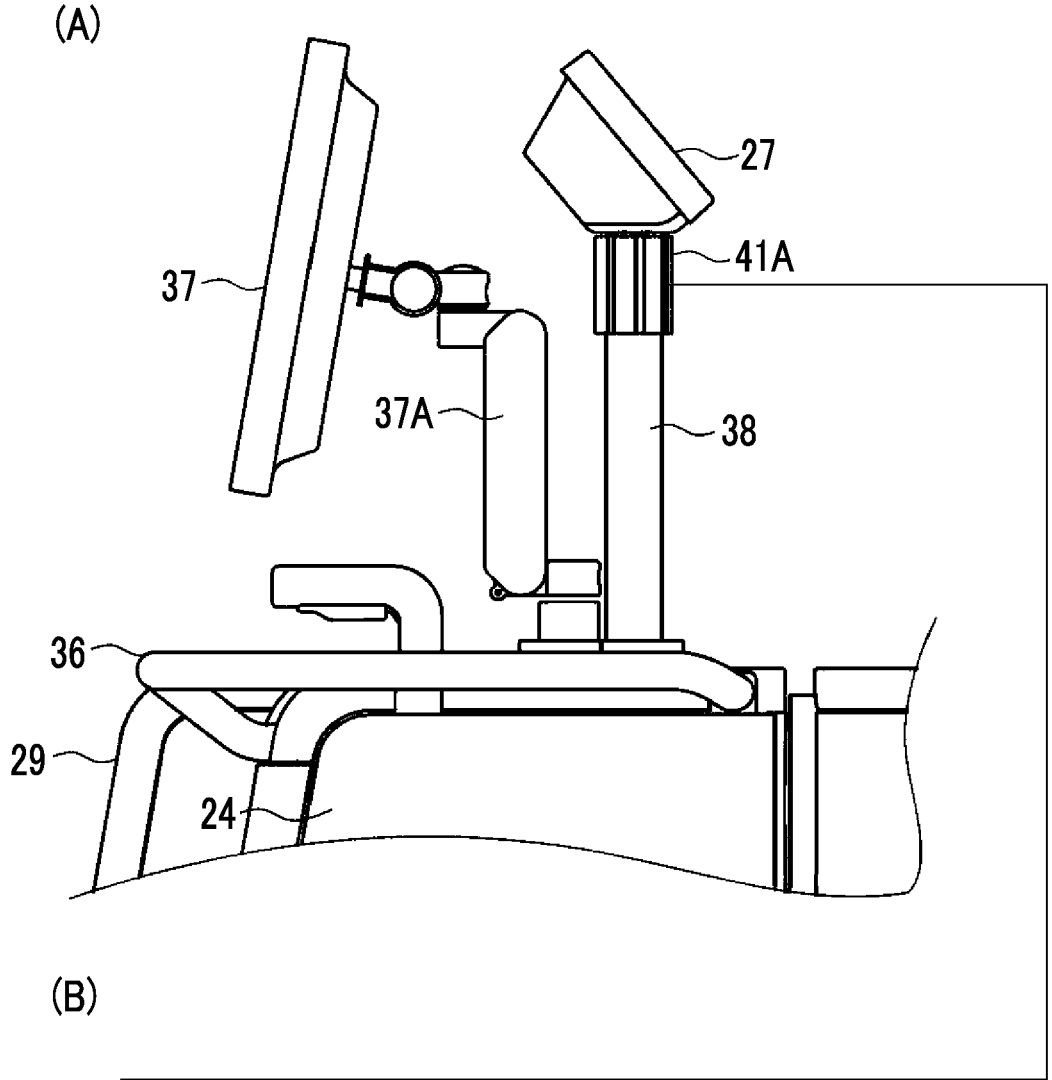
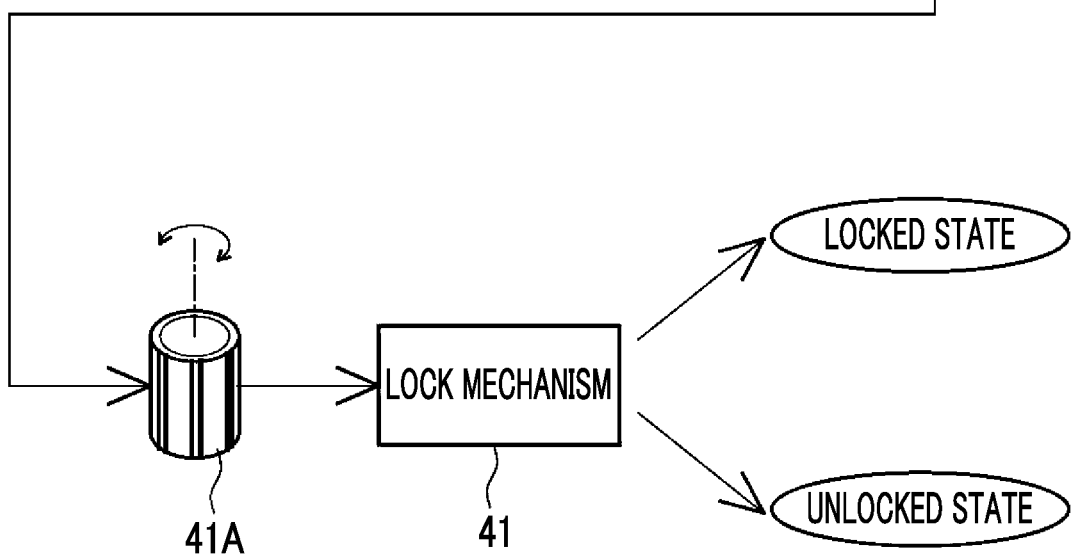

MOBILE RADIOGRAPHY APPARATUS

CROSS-REFERENCE TO RELATED APPLICATIONS

The present application claims priority under 35 U.S.C. § 119 to Japanese Patent Application No. 2021-069372 filed on Apr. 15, 2021. The above application is hereby expressly incorporated by reference, in its entirety, into the present application.

BACKGROUND

1. Technical Field

The technology of the present disclosure relates to a mobile radiography apparatus.

2. Description of the Related Art

A radiography apparatus that captures a radiation image of a subject is known in the medical field (see WO2006/101231A). The radiography apparatus disclosed in WO2006/101231A comprises a portable radiation image detector and a console that displays a radiation image detected by the radiation image detector. In addition, the radiation image detector is provided with an antenna that wirelessly transmits the radiation image to the console.

SUMMARY

Among the radiography apparatuses, there is a mobile radiography apparatus used for, for example, motion picture capturing during surgery. Such a mobile radiography apparatus comprises an arm that holds a radiation source that generates radiation and a radiation image detector, a body part to which the arm is rotatably attached, and a carriage on which the body part is mounted. The arm has, for example, a so-called C-arm having a C-shape, and the radiation source and the radiation image detector are provided at both ends of the C-arm, respectively.

It is conceivable to provide the antenna that wirelessly transmits the radiation image to an external apparatus in the mobile radiography apparatus having such a rotatable arm. It is preferable that the antenna be provided at a position at which a radio wave emitted toward the external apparatus of a communication partner is not easily blocked. Since an upper end of the arm that holds the radiation source and the radiation image detector is positioned at a relatively high position, it is conceivable to provide the antenna at the upper end of the arm. However, at this position, a relative position between the external apparatus and the antenna is changed due to the rotation of the arm, so that there is a problem that stable communication is difficult.

In addition, the mobile radiography apparatus is moved by traveling of the carriage. Therefore, simply fixing the antenna to a location other than the arm cannot handle the change in the relative position between the external apparatus and the antenna in a case in which the carriage travels, and there is still the problem that stable communication is difficult.

WO2006/101231A discloses that the antenna is provided in the portable radiation image detector, but there is not disclosure or suggestion regarding providing the antenna in the mobile radiography apparatus and a problem of providing the antenna in the mobile radiography apparatus.

The technology of the present disclosure provides a mobile radiography apparatus capable of performing relatively stable wireless communication even in a case in which the mobile radiography apparatus is moved due to traveling of a carriage or an arm is rotated.

A mobile radiography apparatus according to the technology of the present disclosure comprises a radiation source, a radiation image detector that detects a radiation image of a subject by receiving radiation emitted from the radiation source and transmitted through the subject, an arm that holds the radiation source and the radiation image detector, a body part to which the arm is rotatably attached, a carriage on which the body part is mounted, and an antenna that emits a radio wave for wirelessly communicating with an external apparatus, the antenna being provided in a portion in which a radiation direction of the radio wave is not changed even in a case in which the arm is rotated and capable of changing the radiation direction of the radio wave.

A frequency band of the radio wave may be a 60 GHz band.

The arm may be a C-arm having a C-shape as viewed in a side view.

The antenna may be provided on an upper surface side of the body part.

The mobile radiography apparatus may further comprise a support part that rotatably supports the arm, the support part being disposed on an upper portion side of the body part and capable of being raised and lowered with respect to the body part, in which the antenna is provided on the support part.

The radiation direction in which the antenna emits the radio wave may be inclined upward with respect to a horizontal direction, and in a case in which an inclined angle with respect to the horizontal direction is defined as α, α may satisfy Conditional Expression (1).

$$0° < \alpha < 90° \quad \text{Conditional Expression (1)}$$

The inclined angle may be fixed at an angle at which the radio wave is not blocked by the arm.

The inclined angle of the antenna may be variable.

The antenna may be attached to an antenna support column extending above the body part from an upper surface side of the body part.

An upper end of the antenna may be lower than a highest reachable position at which one end of the arm is reachable.

The antenna may be rotatable around an axis extending in a vertical direction.

In a case in which a position at which the arm is present in the radiation direction of the radio wave of the antenna is defined as a reference position, a rotation angle range of the antenna may be within a range of ±90° with respect to the reference position.

The mobile radiography apparatus may further comprise a console monitor used for an operation, in which the antenna is displaceable within a range that does not physically interfere with the console monitor.

The mobile radiography apparatus may further comprise a lock mechanism that fixes an orientation of the antenna.

The mobile radiography apparatus may further comprise an orientation adjustment mechanism that adjusts an orientation of the antenna based on a change in a position relative to the external apparatus.

The orientation adjustment mechanism may include a sensor that detects a rotation of the body part around an axis extending in a vertical direction, and an actuator that rotates the antenna in an opposite orientation to the body part.

The orientation adjustment mechanism may include a position sensor that detects a position of the external apparatus, and an actuator that causes the orientation of the antenna to follow the position of the external apparatus detected by the position sensor.

The mobile radiography apparatus may further comprise a wired communication device that uses a cable in addition to a wireless communication device that uses the antenna.

A wireless communication device that performs wireless communication using the antenna may be a wireless communication device of a wireless HDMI (registered trademark) standard that uses a radio wave having a frequency band of a 60 GHz band.

The external apparatus may be a mobile monitor apparatus that includes a carriage and is movable by traveling of the carriage.

According to the technology of the present disclosure, it is possible to provide the mobile radiography apparatus capable of performing relatively stable wireless communication even in a case in which the mobile radiography apparatus is moved due to traveling of the carriage or the arm is rotated.

BRIEF DESCRIPTION OF THE DRAWINGS

Exemplary embodiments according to the technique of the present disclosure will be described in detail based on the following figures, wherein:

FIG. 2 is a side view of the mobile radiography apparatus,

FIG. 8 is a view showing a lock mechanism of the antenna.

DETAILED DESCRIPTION

First Embodiment

Figure 1:
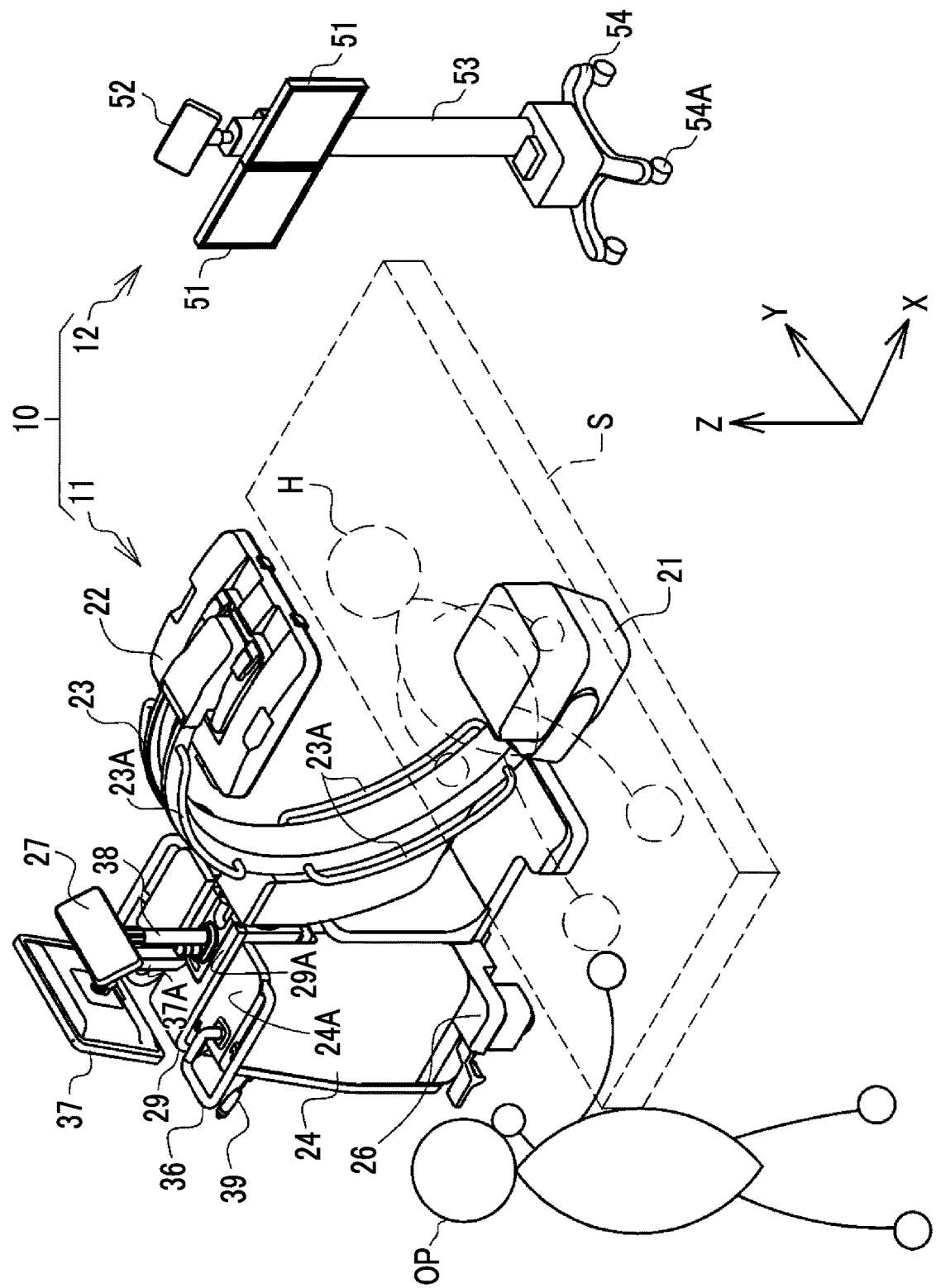
FIG. 1 is an overall perspective view showing a mobile radiography system.

In the following, a mobile radiography system (hereinafter, simply referred to as a radiography system) 10 according to the embodiment of the present disclosure will be described in order with reference to the drawings. As shown in FIG. 1, the radiography system 10 comprises a mobile radiography apparatus (hereinafter, simply referred to as a radiography apparatus) 11 and a mobile monitor apparatus (hereinafter, simply referred to as a monitor apparatus) 12. In the following, in the drawings, an arrow X indicates a front-rear direction of the radiography apparatus 11, an arrow Y indicates a width direction of the radiography apparatus 11, and an arrow Z indicates an up-down direction, which is a vertical direction.

The radiography apparatus 11 is an apparatus that captures a radiation image of a subject H. The radiography apparatus 11 can capture, for example, a motion picture and a still image of the subject H. The motion picture capturing is performed, for example, in a case in which a treatment target part of the subject H is displayed as the motion picture during surgery (also referred to as penetrative imaging). The monitor apparatus 12 is an example of an external apparatus capable of communicating with the radiography apparatus 11, and can display the radiation image of the motion picture or the still image captured by the radiography apparatus 11.

Since both the radiography apparatus 11 and the monitor apparatus 12 are mobile types, it is possible to move each installation location individually or change the orientation. In a case in which any of the radiography apparatus 11 or the monitor apparatus 12 is moved or the like, a relative positional relationship between the radiography apparatus 11 and the monitor apparatus 12 is changed.

The radiography apparatus 11 comprises a radiation source 21, a radiation image detector 22, an arm 23, a body part 24, a carriage 26, and an antenna 27. The monitor apparatus 12 comprises a monitor 51, an antenna 52, a monitor support column 53, and a carriage 54. The antenna 27 and the antenna 52 are used for wirelessly transmitting the radiation image from the radiography apparatus 11 to the monitor apparatus 12. The monitor apparatus 12 includes the carriage 54 and can be moved by traveling of the carriage 54. The carriage 54 has a caster 54A and travels by the rotation of the caster 54A.

As shown in FIGS. 1 and 2, the arm 23 is, for example, a C-arm having a C-shape as viewed in a side view. More precisely, the C-arm is an arm at least partially having an arc shape such that the orbital rotation described below is possible. The arm 23 is attached to the body part 24 to be displaceable. In the following, a side on which the arm 23 is provided is a front side of the radiography apparatus 11, and a side on which the body part 24 is provided is a rear side of the radiography apparatus 11.

The arm 23 has two end portions, the radiation source 21 is provided at one end portion of the arm 23, and the radiation image detector 22 is provided at the other end portion thereof. The arm 23 can hold the radiation source 21 and the radiation image detector 22 in a facing posture. A space into which the subject H and a bed S on which the subject H lies face upward can be inserted is secured between the radiation source 21 and the radiation image detector 22. It should be noted that, in the following, in the side view of the arm 23 (see FIG. 2), with the arm 23 as a reference, a direction in which the radiation source 21 and the radiation image detector 22 are provided may be referred to as a front side the arm 23, and the body part 24 side may be referred to as a rear side the arm 23.

As shown in FIG. 2, in the radiography apparatus 11, the radiation source 21 comprises a radiation tube 21A that generates the radiation and an irradiation field limiting device (also called a collimator or the like) 21B that narrows an irradiation field of the radiation. The radiation is X-rays, for example. The radiation tube 21A generates radiation X by colliding electrons generated from a cathode with an anode. The position at which the electrons collide at the anode is a focus F at which the radiation X is generated.

The radiation image detector 22 detects the radiation image of the subject H by receiving the radiation X emitted from the radiation source 21 and transmitted through the subject H. The radiation image detector 22 comprises a detection panel 22A and a case 22B that accommodates the detection panel 22A. The case 22B can be removed from, for example, the arm 23. The detection panel 22A can be removed from the case 22B, and for example, the type or size of the detection panel 22A accommodated in the case 22B can be changed.

The detection panel 22A is, for example, a flat panel detector (FPD) of a digital radiography (DR) type. The FPD has a detection surface on which a plurality of pixels are two-dimensionally arranged and a thin film transistor (TFT) panel (not shown) for driving the pixels. The detection panel 22A converts the incident radiation into an electric signal and outputs the radiation image showing the subject H based on the converted electric signal. For example, as the detection panel 22A, an indirect conversion type that converts the radiation into visible light using a scintillator and converts the converted visible light into the electric signal is used. It should be noted that the detection panel 22A may be a direct conversion type that directly converts the radiation into the electric signal. In addition, as the radiation image detector 22, a configuration other than a configuration in which the FPD is used as the detection panel 22A may be adopted, for example, a configuration can be adopted in which an image intensifier (I.I) and a camera are combined.

A connecting part 28 disposed on the body part 24 side is attached to the arc-shaped part of the arm 23. The connecting part 28 is attached to a support part 29. Moreover, the support part 29 is attached to the body part 24. In this way, the arm 23 is indirectly attached to the body part 24 via the connecting part 28 and the support part 29.

The arm 23 can be rotated by a manual operation of an operator OP such as a medical practitioner. A handle 23A is provided on the side of the arm 23 along a C-shaped outer shape. The handle 23A is used, for example, in a case of rotating the arm 23.

As for the rotation of the arm 23, first, the arm 23 can be axially rotated around an axis extending in the front-rear direction (axis extending in the X direction in FIG. 2) of the body part 24. The support part 29 extends in the front-rear direction of the body part 24, and internally accommodates a rotation shaft (not shown) for axially rotating the arm 23 to be rotatable. The connecting part 28 disposed in front of the support part 29 is fixed to the rotation shaft and is axially rotated around the shaft together with the arm 23. Inside the support part 29, the rotation shaft is rotated, but a housing itself of the support part 29 accommodating the rotation shaft is not axially rotated.

By this axial rotation, it is possible to reverse the positions of the radiation source 21 and the radiation image detector 22 provided at both ends of the arm 23 in the up-down direction with respect to the subject H. That is, it is possible to change a posture of the arm 23 to a posture in which the radiation source 21 is disposed below the radiation image detector 22, as shown in FIGS. 1 and 2, in contrast, to a posture in which the radiation source 21 is disposed above the radiation image detector 22, as shown in FIG. 3.

Here, since the radiation tube 21A (see FIG. 2) provided in the radiation source 21 is positioned below the subject H, the posture of the arm 23 shown in FIGS. 1 and 2 is called an undertube posture. On the other hand, since the radiation tube 21A is positioned above the subject H, the posture of the arm 23 shown in FIG. 3 is called an overtube posture.

Figure 3:
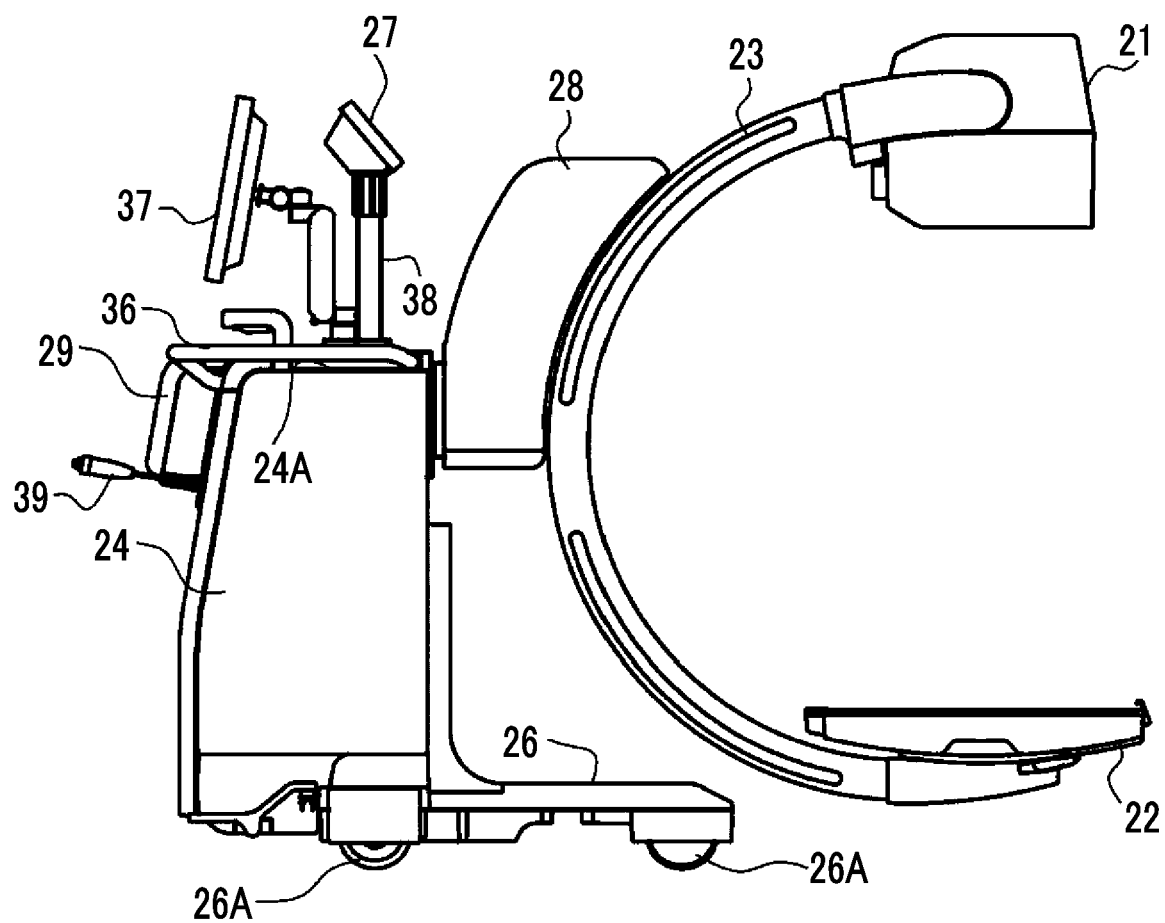
FIG. 3 is a side view of the mobile radiography apparatus in a case in which an arm is axially rotated.

In the overtube posture shown in FIG. 3, the radiation image detector 22 is closer to the position of the bed S than in the undertube posture, and it is possible to widen the distance between the radiation source 21 and the subject H. Therefore, it is possible to image a relatively wide region. Therefore, in many cases, the overtube posture is mainly used for capturing the still image of the subject H. On the other hand, in the undertube posture, since a part of the radiation emitted from the radiation source 21 is blocked by the bed S or the like, it is possible to reduce an exposure dose of the operator OP or the like around the subject H (see FIG. 1). Therefore, in many cases, the undertube posture is used for the motion picture capturing in which the radiation is continuously emitted.

Figure 4:
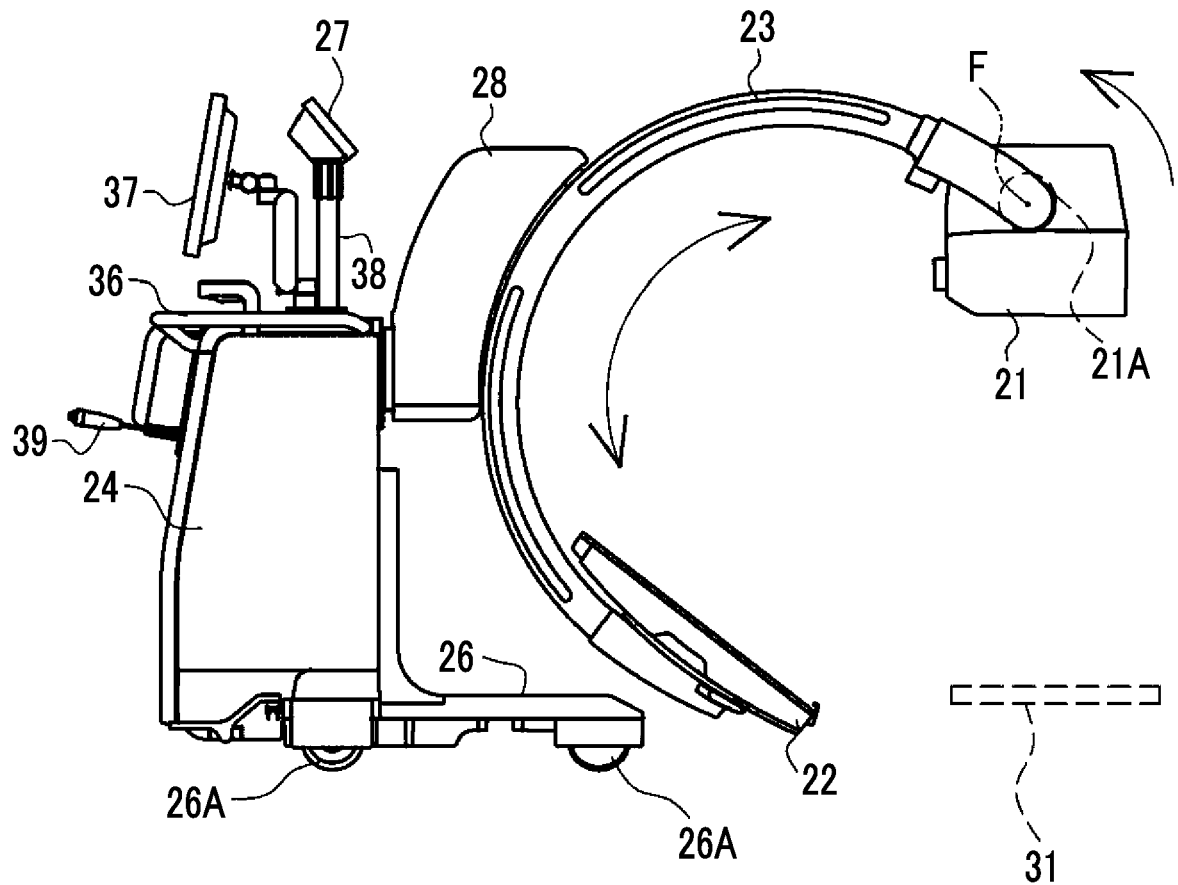
FIG. 4 is a side view of the mobile radiography apparatus in a case in which the arm is orbitally rotated.

In addition, as shown in FIG. 4, the arm 23 can be orbitally rotated. The orbital rotation is a rotation centered on a virtual axis extending in the Y direction with the outer shape of the arc-shaped arm 23 as the orbit. The arm 23 is attached to the connecting part 28 in a state of being capable of being orbitally rotated.

In this way, the rotation of the arm 23 includes two types of rotation, the axial rotation and the orbital rotation. The support part 29 rotatably supports the arm 23. Moreover, since the support part 29 is attached to the body part 24, the arm 23 is indirectly and rotatably attached to the body part 24 via the support part 29.

In addition, the radiation source 21 is rotatably attached to the arm 23 around an axis extending in the Y direction. A rotation center of the radiation source 21 is the focus F of the radiation tube 21A. As shown in FIG. 4, by orbitally rotating the arm 23 and rotating the radiation source 21 with respect to the arm 23, for example, it is possible to dispose a portable radiation image detector (so called electronic cassette) 31 different from the radiation image detector 22 to face the radiation source 21. As a result, instead of the radiation image detector 22, it is possible to perform imaging in which the radiation image detector 31 and the radiation source 21 are combined.

Figure 5:
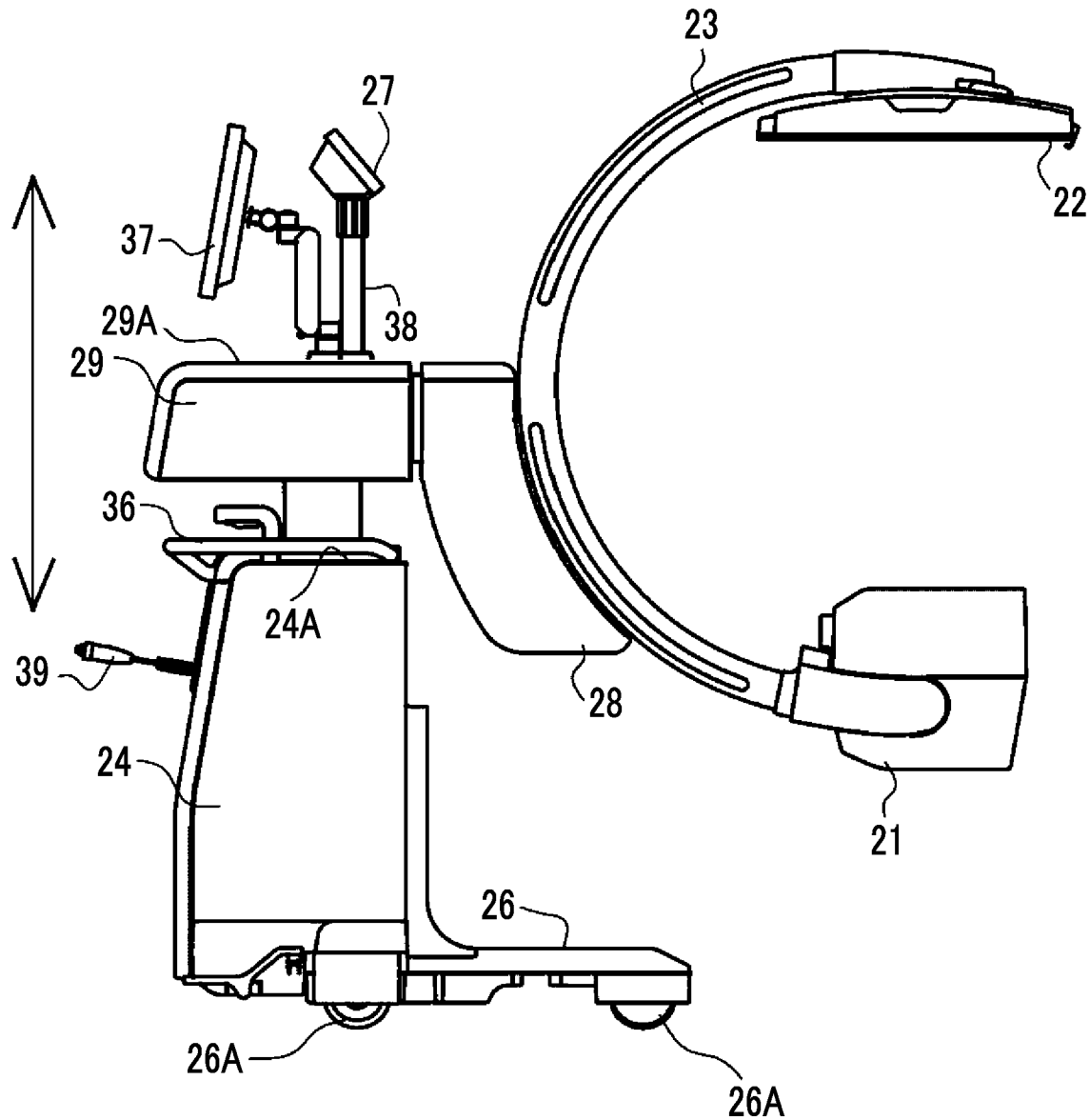
FIG. 5 is a side view of the mobile radiography apparatus in a case in which the arm is raised.

In addition, as shown in FIG. 5, the support part 29 is attached to the body part 24 to be able to be raised and lowered in the up-down direction. Moreover, the arm 23 can be raised and lowered by raising and lowering the support part 29. As shown in FIG. 1 (see also FIG. 6), the support part 29 is disposed on the upper portion side of the body part 24.

As shown in FIGS. 1 and 2, the body part 24 of the radiography apparatus 11 has a vertically long substantially rectangular parallelepiped shape. The rear side of the body part 24 is an inclined surface, and the width of the body part 24 is increased in the front-rear direction from the upper side to the lower side. The body part 24 is mounted on the carriage 26. The carriage 26 has a plurality of casters 26A and can travel on a floor surface 30. In addition, at least some of the casters 26A are steering wheels that revolve. Since the steering wheels are provided, it is possible to easily change the direction in which the carriage 26 travels.

A handle 36 is provided in an upper portion of the body part 24. The handle 36 is gripped by the operator OP and is used in a case of moving the radiography apparatus 11. The handle 36 has a pipe shape as an example, and is provided to surround the side and the rear side of the body part 24.

In addition, an irradiation switch 39 for starting radiography is provided on a rear surface of the body part 24. By operating the irradiation switch 39, an instruction for starting irradiation of the radiation is input. The irradiation switch 39 is attached to the body part 24 via a telescopic cable, for example, and the irradiation switch 39 can be operated at a position away from the body part 24 by extending the telescopic cable.

In addition, a recess for accommodating the support part 29 is formed on an upper surface 24A of the body part 24 at the center in the width direction (that is, the Y direction). The support part 29 has a rectangular tubular shape with the front-rear direction, which is a longitudinal direction, and has an upper surface 29A which is substantially flat similar to the upper surface 24A of the body part 24. In a state in which the support part 29 is accommodated in the recess of the body part 24, the upper surface 24A of the body part 24 and the upper surface 29A of the support part 29 are substantially the same height.

A console monitor 37 is provided on the upper surface 29A of the support part 29. The console monitor 37 is an example of a console monitor used for an operation. On a display screen of the console monitor 37, an operation screen for setting the radiography apparatus 11 and the like is displayed, and it is also possible to display the radiation image captured by the radiography apparatus 11. Examples of the setting of the radiography apparatus 11 include irradiation conditions, such as a tube voltage of the radiation tube 21A, a tube current, and an irradiation time of the radiation. In a case of the motion picture capturing, basically, the irradiation time is not set, and after an instruction for starting the motion picture capturing is given, the motion picture capturing is continued until an instruction for termination is input.

The console monitor 37 is attached to the upper surface 29A of the support part 29 via a support arm 37A. The support arm 37A can be rotated around an axis extending in the up-down direction (that is, the Z direction). As a result, the console monitor 37 can be rotated around an axis extending in the Z direction. At an initial position of the console monitor 37, the display screen faces the rear side of the body part 24. In addition, the console monitor 37 is rotatably attached around an axis extending in the Y direction, as a result, it can also be tilted.

In addition, the antenna 27 is provided on the upper surface 29A of the support part 29 in addition to the console monitor 37. As described above, the antenna 27 is an antenna for wireless communication that emits radio waves for wirelessly communicating with the monitor apparatus 12 which is an example of an external apparatus. The antenna 27 is an example of an antenna of the present disclosure. The antenna 27 is provided on the upper surface 29A via an antenna support column 38 extending in the up-down direction (that is, the Z direction). In this way, the antenna 27 is provided on the upper surface 24A side of the body part 24. In addition, a lower end of the antenna support column 38 is attached to the upper surface 29A of the support part 29, and extends above the body part 24. That is, the antenna 27 is attached to the antenna support column 38, which is an example of a support column extending above the body part 24 from the upper surface 24A side of the body part 24. In addition, the support part 29 is an example of a portion in which a radiation direction RD of the radio waves is not changed even in a case in which the arm 23 is rotated.

As shown in FIG. 2, an upper end of the antenna 27 is lower than a highest reachable position at which one end of the arm 23 can reach. That is, in a case in which a height of the upper end of the antenna 27 is defined as T1 and the highest reachable position of the arm 23 is defined as T0 in FIG. 2, a relationship between T1 and T0 is T1<T0.

As shown in FIG. 5, the arm 23 can be raised and lowered together with the support part 29. Moreover, in the present example, since the antenna 27 is provided on the support part 29 of the arm 23, the antenna 27 is also raised and lowered as the arm 23 is raised and lowered. Therefore, in the present example, even in a case in which the arm 23 is raised and lowered, the relationship T1<T0 between the highest reachable position T0 of the arm 23 and the height T1 of the upper end of the antenna 27 is not changed. That is, a relative height of the antenna 27 to the arm 23 is not changed.

In addition, the portion to which the antenna 27 is attached is the support part 29, and the support part 29 is not displaced even in a case in which the arm 23 is rotated (orbital rotation or axial rotation). That is, the antenna 27 is provided in the portion in which the radiation direction of the radio waves is not changed even in a case in which the arm 23 is rotated. In addition, as will be described below, the antenna 27 can change the radiation direction RD of the radio waves independently of the rotation of the arm 23.

In the present example, the antenna 27 emits the radio waves obtained by modulating the radiation image captured by the radiography apparatus 11. By the monitor apparatus 12 receiving the radio waves emitted by the antenna 27, the monitor apparatus 12 can display the radiation image. The monitor apparatus 12 is an apparatus independent of the radiography apparatus 11 and can be moved. Therefore, for example, as shown in FIG. 1, it is possible to dispose the monitor apparatus 12 at a distance from the radiography apparatus 11, and it is possible to dispose the monitor apparatus 12 at a position at which the operator OP such as the medical practitioner can easily visually recognize.

In a case in which the monitor apparatus 12 is moved, the relative position between the radiography apparatus 11 and the monitor apparatus 12 is changed. As a result, the relative position between the antenna 27 of the radiography apparatus 11 and the antenna 52 of the monitor apparatus 12 is also changed. As a result, the radio wave intensity of the radio waves transmitted and received between the antenna 27 and the antenna 52 may be changed, or a shield (including a person) that blocks the radio waves may enter between the antenna 27 and the antenna 52. In such a case, a communication quality of the wireless communication can be made stable by changing the orientation in which the radio waves of the antenna 27 are emitted.

As shown in FIG. 2, at the initial position, the antenna 27 is disposed in a posture in which the radiation direction RD of the radio waves faces the front side of the body part 24. The antenna 27 of the present example is a plate-shaped antenna in which a radiation surface of the radio waves is formed of a flat surface, and the radiation surface faces the front side at the initial position. Here, the radiation direction RD is a direction representing a traveling direction of the radio waves, and in a case in which the radio waves have a spread angle that spreads from the radiation surface, is a direction matching the center of the spread angle.

Further, the radiation direction RD in which the antenna 27 emits the radio waves is inclined upward with respect to a horizontal direction HL (direction parallel to the XY plane in FIG. 2). In a case in which the inclined angle with respect to the horizontal direction HL is defined as α, in the present example, the inclined angle α is 45° and the inclined angle α is fixed. By inclining the radiation direction RD of the radio waves of the antenna 27 upward by 45° with respect to the horizontal direction HL, the radio waves can be emitted toward a ceiling 56, for example. The radio waves that reach the ceiling 56 are reflected by the ceiling 56. By setting the inclined angle α to 45°, it is possible to transmit the radio waves to the monitor apparatus 12 by using the reflection by the ceiling 56.

In addition, the inclined angle α is fixed at an angle at which the radio waves are not blocked by the arm 23. The inclined angle α of 45° in the present example is an example of the angle at which the radio waves are not blocked by the arm 23. As shown in FIG. 2, in a case in which the inclined angle α is 45°, the radio waves emitted by the antenna 27 travel above the arm 23 disposed in front of the antenna 27, so that the radio waves are not blocked by the arm 23.

In addition, the antenna 27 is attached to the antenna support column 38 extending above the body part 24 from the upper surface 24A side of the body part 24. By attaching the antenna 27 to the antenna support column 38, the antenna 27 can be disposed at a position higher than the upper surface 24A of the body part 24.

Figure 6:
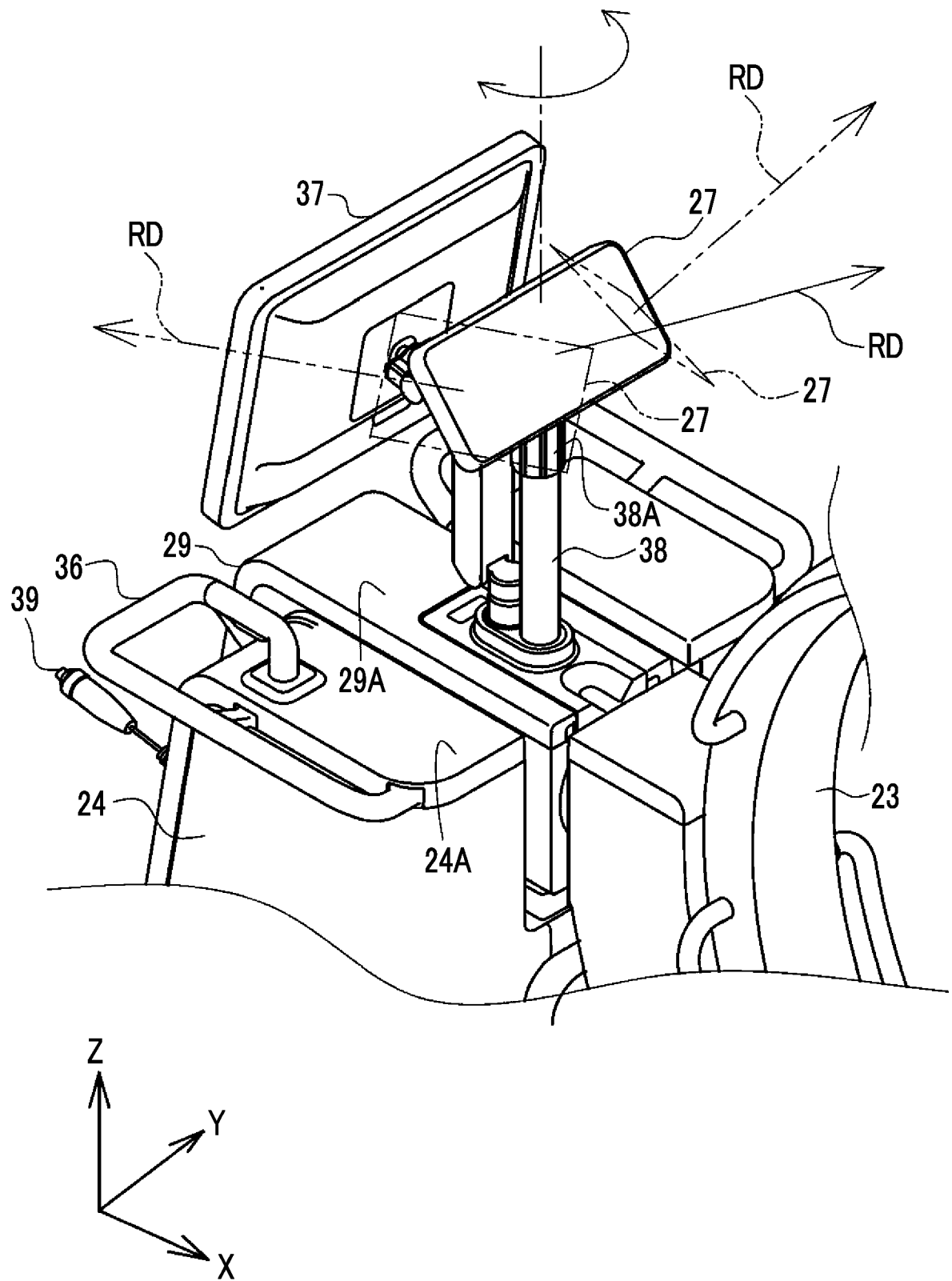
FIG. 6 is a perspective view of an antenna.
Figure 7:
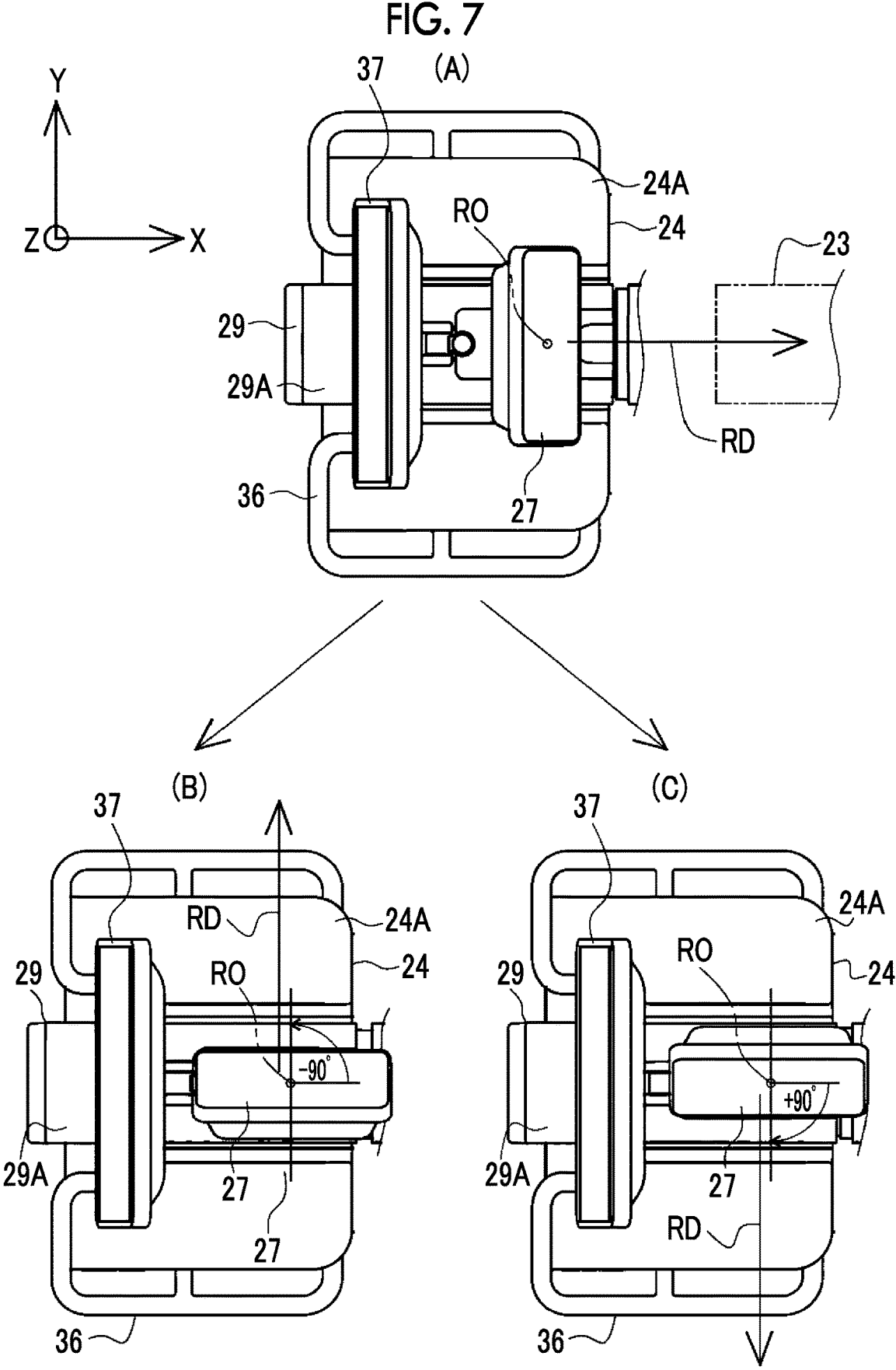
FIG. 7 is a view showing a rotation range of the antenna.

As shown in FIGS. 6 and 7, the antenna 27 can be rotated around the axis extending in the up-down direction, which is the vertical direction. A rotation center RO of the antenna 27 matches, for example, a central axis of the antenna support column 38. As shown in FIG. 7, in a plan view, in a case in which a position at which the arm 23 is present in the radiation direction RD of the radio waves of the antenna 27 is defined as a reference position, a rotation angle range of the antenna 27 is within a range of ±90° with respect to the reference position. In the present example, a position shown in (A) of FIG. 7 is the reference position at which the arm 23 is present in the radiation direction RD of the radio waves of the antenna 27 in a case in which the radiography apparatus 11 is viewed in a plan view. More specifically, the reference position is a position at which the radiation direction RD of the radio waves of the antenna 27 is parallel to the front-rear direction of the body part 24. With respect to this reference position, the antenna 27 can be rotated within a range of a position of −90° shown in (B) of FIG. 7 and a position of +90° shown in (C) of FIG. 7. As a result, it is possible to adjust the orientation of the antenna 27 in a case in which the relative position between the radiography apparatus 11 and the monitor apparatus 12 is changed.

Both the antenna 27 and the console monitor 37 are attached to the upper surface 29A of the support part 29, and are disposed side by side in the front-rear direction of the body part 24. As shown in FIG. 7, at least in a state in which the console monitor 37 is at the initial position (position at which the display screen faces the rear side), the antenna 27 can be displaced within a range that does not physically interfere with the console monitor 37. Specifically, the antenna 27 is disposed at a distance from the console monitor 37 at the initial position such that the console monitor 37 does not enter the rotation range of the antenna 27.

In addition, the antenna 27 is disposed behind the arm 23, and the distance between the antenna 27 and the arm 23 in the front-rear direction of the body part 24 is fixed. Therefore, the antenna 27 is disposed at a position that also does not physically interfere with the arm 23.

In addition, as shown in FIG. 8, a lock mechanism 41 that fixes the orientation of the antenna 27 is provided. The lock mechanism 41 fixes the orientation of the antenna 27 at any position within the rotation range of the antenna 27 shown in FIG. 7. (A) of FIG. 8 is a side view of the antenna 27 and the antenna support column 38, and (B) of FIG. 8 is a conceptual diagram of the lock mechanism 41. The lock mechanism 41 has a rotation operating part 41A provided on the antenna support column 38. The lock mechanism 41 can be switched between a locked state in which the orientation of the antenna 27 is fixed and an unlocked state in which the antenna 27 is unlocked and caused to be rotated, by rotating the rotation operating part 41A by a manual operation. In the lock mechanism 41, for example, in a case in which the rotation operating part 41A is rotated, the frictional resistance of the rotation shaft that rotates the antenna 27 is changed. It is a mechanism to switch between the locked state and the unlocked state by a change in this frictional resistance. It should be noted that an electric mechanism using an actuator may be used as the lock mechanism 41.

Figure 9:
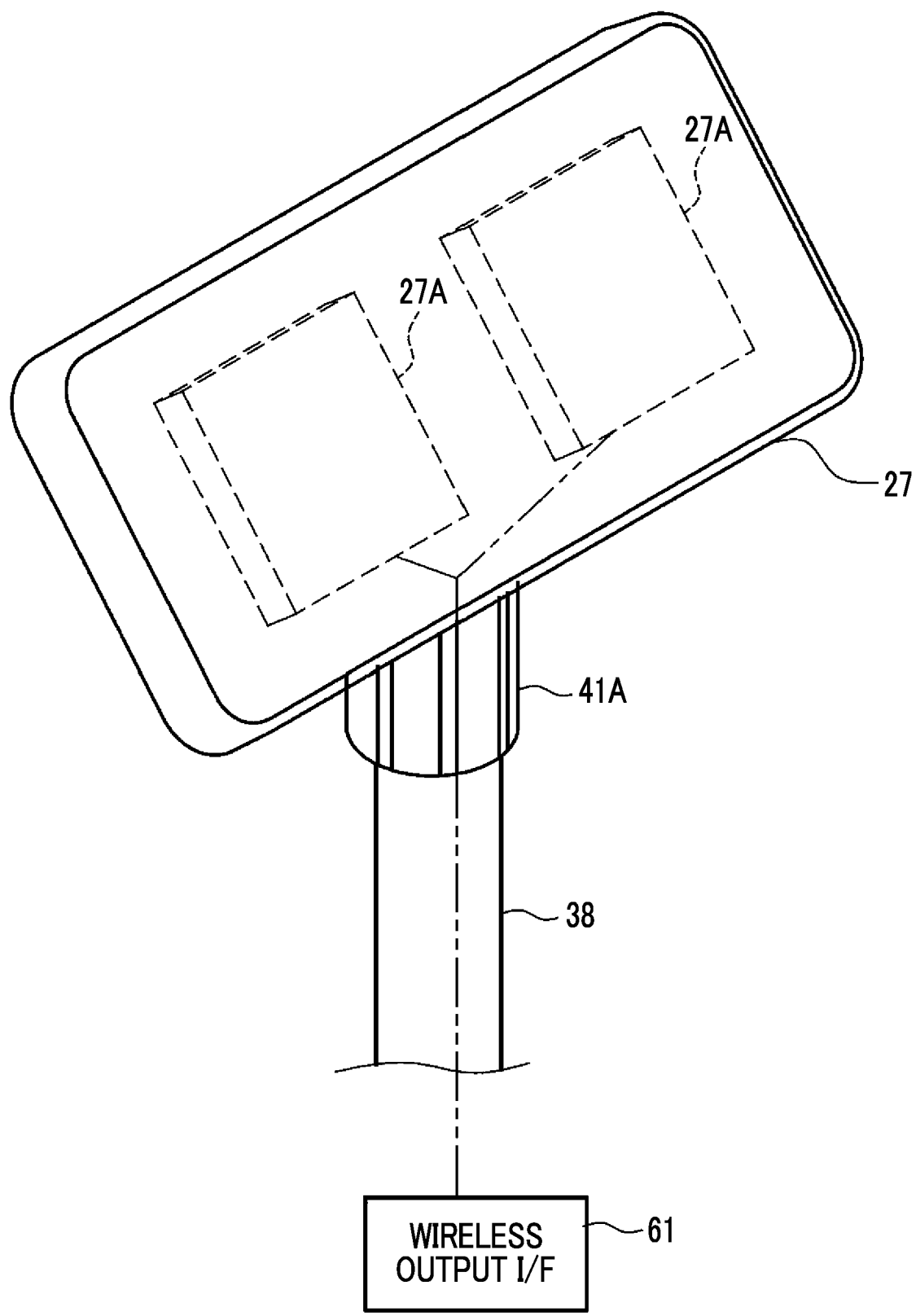
FIG. 9 is an enlarged perspective view of an antenna of a mobile monitor apparatus.

As shown in FIG. 9, the antenna 27 includes, for example, two antenna units 27A. Including two antenna units 27A enables, for example, multiple-input and multiple-output (MIMO) wireless communication. As a result, the communication quality and throughput of wireless communication are improved.

The antenna unit 27A is connected to a wireless output inter/face (I/F) 61. The wireless output I/F 61 is an example of a wireless communication device that performs wireless communication using the antenna 27. In the present example, the wireless output I/F 61 is a wireless communication device of the wireless high-definition multimedia interface (HDMI) (registered trademark) standard that uses the radio waves having the frequency band of the 60 GHz band. The wireless output I/F 61 is composed of a modulation circuit that modulates a video signal into the radio waves and outputs the modulated radio waves, a communication circuit that performs transmission control according to a communication protocol, and the like.

Figure 10:
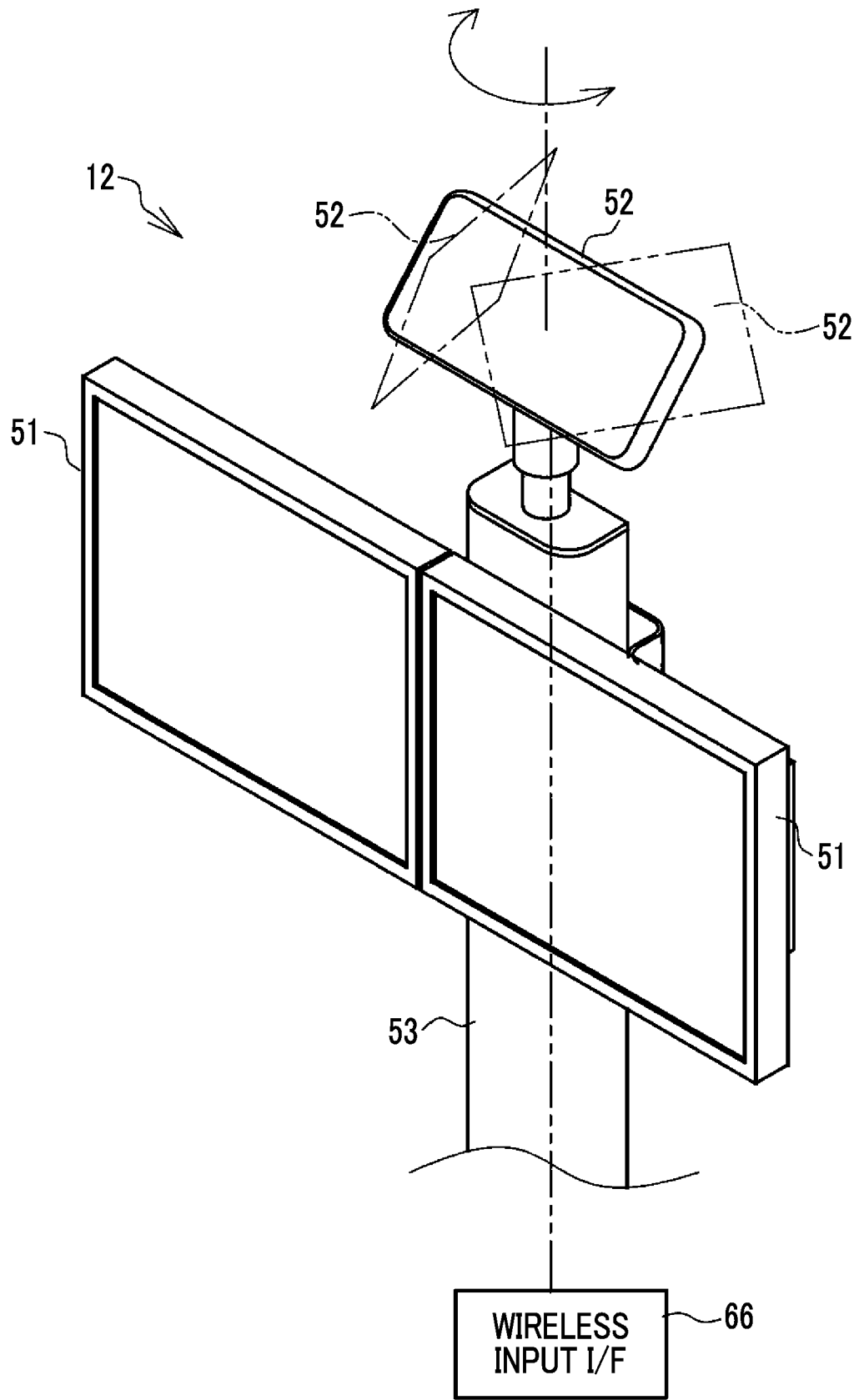
FIG. 10 is an enlarged perspective view of the mobile monitor apparatus.

As shown in FIG. 10, the monitor apparatus 12 comprises two monitors 51. Therefore, it is possible to display the motion picture on one monitor 51 and the still image on the other monitor 51. The still image may be a still image captured by the radiography apparatus 11 or a still image read from an image server (not shown).

The antenna 52 of the monitor apparatus 12 also includes two built-in antenna units 52A (see FIG. 11) having the same standard as the antenna units 27A of the antenna 27. The antenna 52 is used for receiving the radio waves from the antenna 27. The antenna unit 52A is connected to a wireless input inter/face (I/F) 66. The wireless input I/F 66 is an example of a wireless communication device that performs wireless communication using the antenna 52. In the present example, since the wireless input I/F 66 is for communicating with the wireless output I/F 61, it is a wireless communication device of the wireless high-definition multimedia interface (HDMI) (registered trademark) standard that uses the radio waves having the frequency band of the 60 GHz band, similar to the wireless output I/F 61.

The antenna 52 can be displaced with respect to the monitor support column 53. Specifically, the antenna 52, similar to the antenna 27, can be rotated around an axis extending in the up-down direction. As a result, it is possible to adjust the orientation of the antenna 52 in a case in which the relative position between the radiography apparatus 11 and the monitor apparatus 12 is changed.

In addition, a receiving surface of the antenna 52 that receives the radio waves is inclined with respect to the horizontal direction HL. The inclined angle of the antenna 52 is set to 45°, which is an angle corresponding to the inclined angle α of the antenna 27.

In addition, the antenna 52 is disposed above the monitor 51. In many cases, there is a shield that blocks the radio waves around the monitor apparatus 12. In order to avoid such a shield, the height at which the antenna 52 is disposed is preferably high. In addition, by disposing the antenna 52 above the monitor 51, it is possible to prevent the radio waves from being blocked by the monitor 51.

Figure 11:
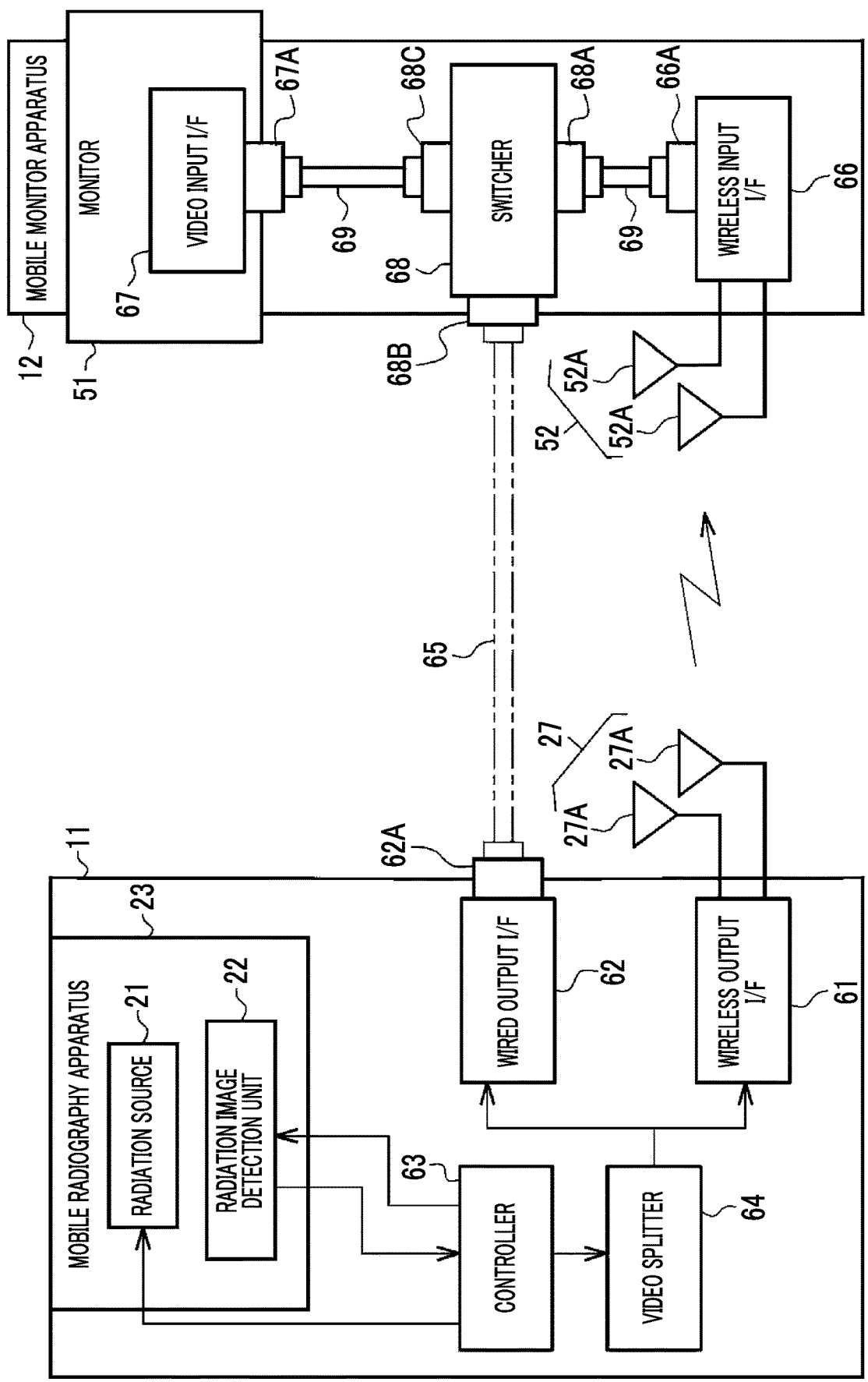
FIG. 11 is a functional block diagram relating to communication of the mobile radiography system.

As shown in FIG. 11, the radiography apparatus 11 comprises a wired output I/F 62 which is an example of a wired communication device using a connection cable 65, in addition to the wireless output I/F 61 using the antenna 27. The wired output I/F 62 includes a connector 62A for connecting the connection cable 65. The standard of the connector 62A has, for example, a digital visual interface (DVI) standard. It is needless to say that the standard of the connector 62A may be another standard such as the HDMI (registered trademark) standard.

Further, the radiography apparatus 11 comprises a controller 63 and a video splitter 64. The controller 63 comprehensively controls the units of the radiography apparatus 11 in addition to the radiation source 21 and the radiation image detector 22. The controller 63 acquires the radiation image detected by the radiation image detector 22. The controller 63 outputs the video signal of the acquired radiation image to the video splitter 64. The video splitter 64 outputs the video signal to be transmitted to the monitor apparatus 12 to both the wireless output I/F 61 and the wired output I/F 62.

The monitor apparatus 12 comprises a switcher 68 in addition to the wireless input I/F 66. In addition, the monitor 51 comprises a video input I/F 67. A connector 66A of the wireless input I/F 66 has, for example, the HDMI (registered trademark) standard, and a connector 67A of the video input I/F 67 has, for example, the DVI standard.

The switcher 68 is disposed on a connection path connecting the monitor 51 and the antenna 52, and selectively outputs, to the monitor 51, the video signal input from the antenna 52 and the video signal input from the wired output I/F 62 of the radiography apparatus 11. The switcher 68 includes connectors 68A, 68B, and 68C. The connectors 68A, 68B, and 68C have, for example, the DVI standard similar to the connector 67A of the video input I/F 67.

An internal cable 69 extending from the connector 66A of the wireless input I/F 66 is connected to the connector 68A. The connection cable 65 for connecting to the wired output I/F 62 of the radiography apparatus 11 is connected to the connector 68B. The internal cable 69 connected to the connector 67A of the video input I/F 67 is connected to the connector 68C. The connector 68A and the connector 68B are input ports to which the video signal is input, and the connector 68C is an output port from which the video signal input to the connector 68A or the connector 68B is output.

The switcher 68 switches an input source of the video signal displayed on the monitor 51 to any of the wireless output I/F 61 or the wired output I/F 62 by switching an electrical connection destination with the connector 68C between the connector 68A and the connector 68B. The switcher 68 monitors, for example, the video signal input from the wireless output I/F 61 to the connector 68A, and automatically switches the input source of the video signal to the connector 68B in a case in which the input of the video signal to the connector 68A is interrupted or failed. Therefore, even in a case in which a wireless communication failure occurs, in a case in which the connection cable 65 is connected by the operator OP, the display of the radiation image on the monitor apparatus 12 can be restarted by wired communication.

Action and Effect

As described above, the radiography apparatus 11 comprises the radiation source 21, the radiation image detector 22 that detects the radiation image of the subject H by receiving the radiation X emitted from the radiation source 21 and transmitted through the subject H, the arm 23 that holds the radiation source 21 and the radiation image detector 22, the body part 24 to which the arm 23 is attached to be displaceable, the carriage 26 on which the body part 24 is mounted, and the antenna 27 that emits the radio waves for wirelessly communicating with the monitor apparatus 12, which is an example of the external apparatus, the antenna being provided in the portion in which the radiation direction RD of the radio waves is not changed even in a case in which the arm 23 is rotated and capable of changing the radiation direction RD of the radio waves.

Therefore, it is possible to perform relatively stable wireless communication even in a case in which the radiography apparatus 11 is moved due to traveling of the carriage 26 or the arm 23 is rotated. That is, the antenna 27 is provided in the portion in which the radiation direction RD of the radio waves is not changed even in a case in which the arm 23 is rotated. Therefore, even in a case in which the arm 23 is rotated, the relative position between the monitor apparatus 12 and the antenna 27 is not changed. In addition, as shown in FIG. 7, the antenna 27 can change the radiation direction RD of the radio waves. Therefore, even in a case in which the radiography apparatus 11 is moved due to the traveling of the carriage 26, it is possible to make the radiation direction RD of the radio waves of the antenna 27 correspond to the change in the relative position between the antenna 27 and the monitor apparatus 12. It is needless to say that it is also possible to handle the change in the relative position between the antenna 27 and the monitor apparatus 12 by moving only the monitor apparatus 12 without changing the position of the radiography apparatus 11, or changing the orientation of the radiography apparatus 11 or the monitor apparatus 12. As a result, it is possible to perform stable wireless communication as compared with a case in which the radiation direction RD of the antenna 27 cannot be changed. Since the radiography apparatus 11 is a mobile type, the position relative to the monitor apparatus 12 is likely to be changed, and thus the technology of the present disclosure is particularly effective.

Figure 12:
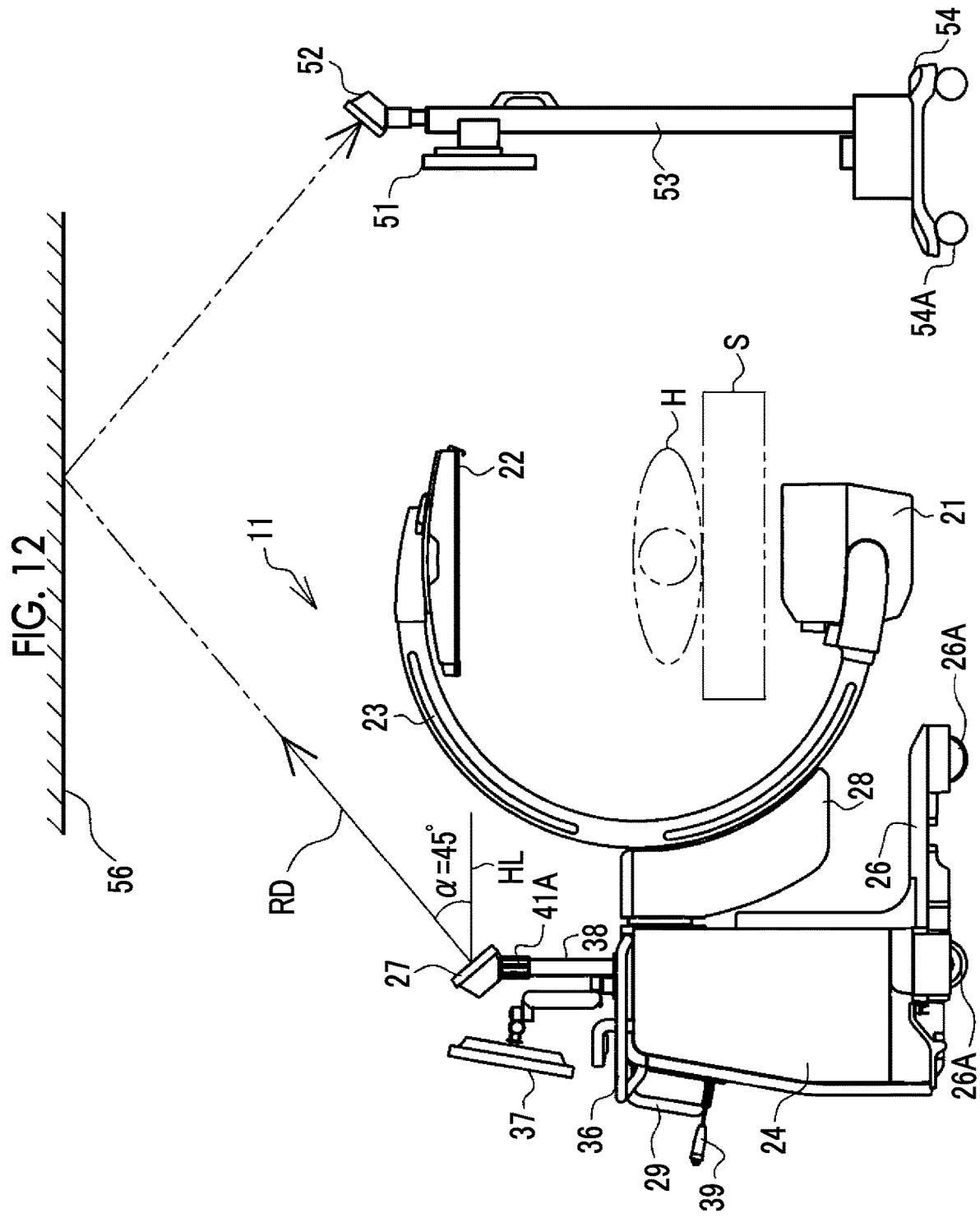
FIG. 12 is a view showing an example of a positional relationship between a mobile radiography apparatus and the mobile monitor apparatus.

As an example of a relative positional relationship between the radiography apparatus 11 and the monitor apparatus 12, as shown in FIG. 12, the monitor apparatus 12 may be disposed to face the front surface of the radiography apparatus 11 with the bed S interposed therebetween. In the case shown in FIG. 12, the orientation of the antenna 27 of the radiography apparatus 11 is set to the reference position shown in (A) of FIG. 7, and the radiation direction RD of the radio waves is directed to the front side of the body part 24 in a plan view. As a result, the antenna 27 of the radiography apparatus 11 and the antenna 52 of the monitor apparatus 12 can face each other in a plan view (that is, in an XY plane).

Figure 13:
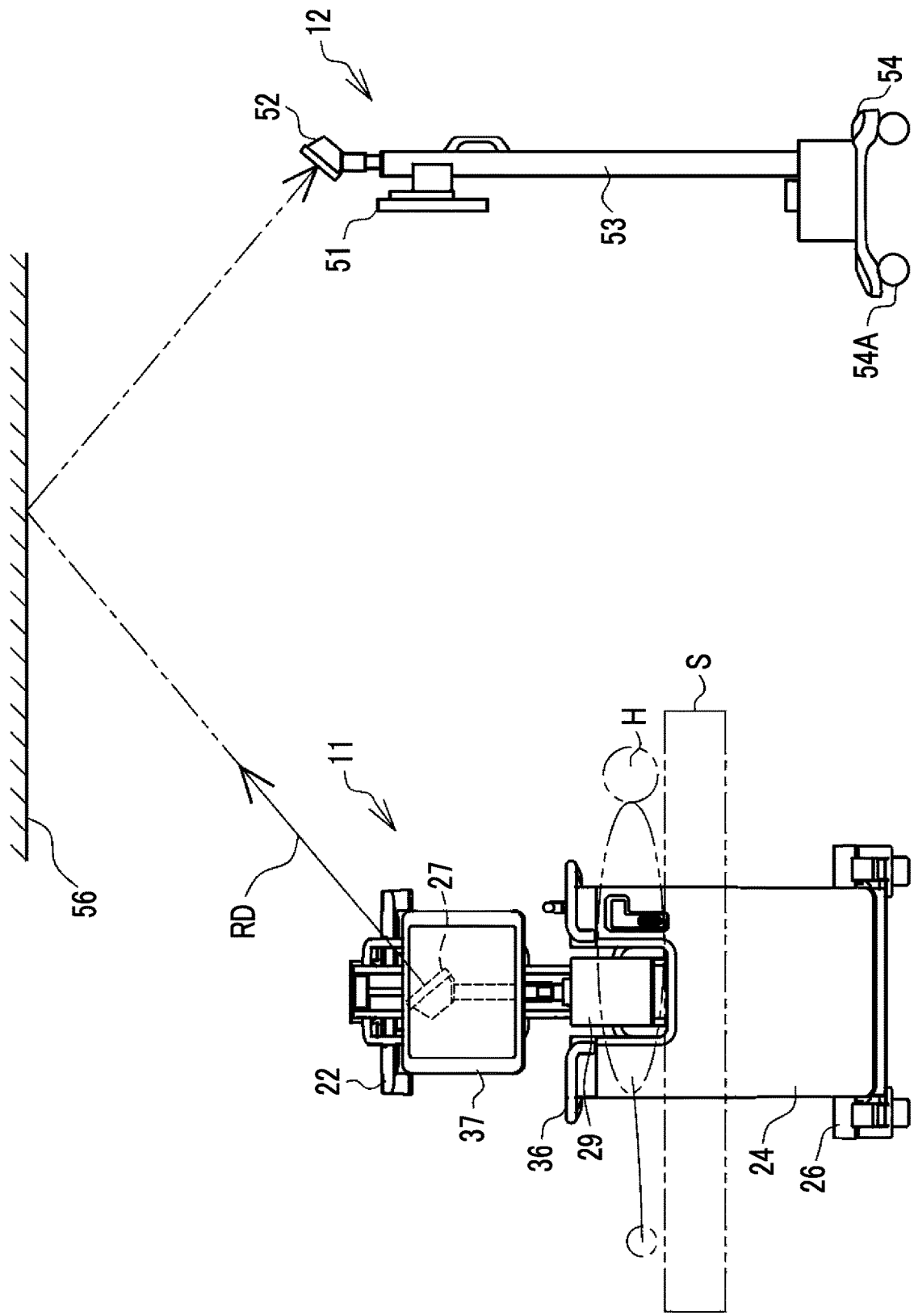
FIG. 13 is a view showing another example of the positional relationship between the mobile radiography apparatus and the mobile monitor apparatus.

In addition, as another example, as shown in FIG. 13, the monitor apparatus 12 may also be disposed on the right side of the radiography apparatus 11. In this case, as shown in (C) of FIG. 7, the orientation of the antenna 27 is set to a position of +90° with respect to the reference position, and the radiation direction RD of the radio waves is directed to the right side of the body part 24 in a plan view. As a result, the antenna 27 of the radiography apparatus 11 and the antenna 52 of the monitor apparatus 12 can face each other in a plan view.

In a case in which the radio waves are transmitted and received, the communication quality is stable in a state in which the antenna 27 on the transmission side and the antenna 52 on the reception side face each other as compared with a state in which the antenna 27 on the transmission side and the antenna 52 on the reception side do not face each other. In particular, as the frequency band of the radio waves is higher, the straightness of the radio waves is stronger, so that it is necessary to make the antennas face each other. Therefore, the technology of the present disclosure is more effective as the frequency band is higher.

It should be noted that, in the present example, the support part 29 has been described as an example of the portion in which the radiation direction RD of the radio waves is not changed even in a case in which the arm 23 is rotated, but the portion in which the radiation direction RD of the radio waves is not changed even in a case in which the arm 23 is rotated may be a portion other than the support part 29 and, for example, may be the upper surface 24A of the body part 24. It should be noted that, since the support part 29 is raised and lowered together with the arm 23 with respect to the body part 24, it is preferable to provide the antenna 27 on the support part 29. The reason for the above is that there are merits that the antenna 27 can be disposed at a position higher than the body part 24 in the support part 29, and the relative height between the antenna 27 and the arm 23 is not changed even in a case in which the arm 23 is raised and lowered.

In addition, in the antenna 27 of the present example, the radiation direction RD of the radio waves is inclined upward by 45° with respect to the horizontal direction, and the receiving surface of the antenna 52 is also inclined upward by 45° with respect to the horizontal direction HL. Therefore, by facing the antenna 27 and the antenna 52 in a plan view (that is, in the XY plane), the radio waves emitted by the antenna 27 can be reflected by the ceiling 56 to be transmitted to the antenna 52.

In general, the number of shields that block the radio waves tends to be larger as the distance to the floor surface 30 (see FIG. 2) is shorter, and the number of shields that block the radio waves tends to be smaller as the distance to the ceiling 56 is shorter. By emitting the radio waves upward from the antenna 27 of the radiography apparatus 11 with respect to the horizontal direction HL and using the reflection of the radio waves by the ceiling 56, it is possible to transmit the radio waves to the monitor apparatus 12 disposed at a distance while avoiding the shield.

In the present example, the frequency band of the radio waves emitted by the antenna 27 is the 60 GHz band. Since the radio waves having the frequency bands such as a 2.4 GHz band and a 5 GHz band used in the wireless local area network (LAN) standard are used in many various communication devices such as a tablet terminal and a wireless access point, the radio wave interference is likely to occur.

By using the radio waves having the 60 GHz band, the radio wave interference is suppressed, so that the communication quality of wireless communication is stable. In addition, by using the radio waves having the 60 GHz band, the transmission amount per unit time can be increased as compared with the radio waves having the 2.4 GHz band and the 5 GHz band. Therefore, the radio waves having the 60 GHz band are suitable for transmitting the motion picture having a large amount of data. In a case in which the motion picture is transmitted, there is often a concern about display delay in a case of the radio waves having the 2.4 GHz band and the 5 GHz band, but in a case of the radio waves having the 60 GHz band, the concern about display delay can be reduced.

In addition, as described above, as the frequency band of the radio waves is higher, the straightness of the radio waves is stronger, and it is more easily affected by the shield. Therefore, the technology of the present disclosure is particularly effective in a case in which the frequency band of the 60 GHz band, which has stronger straightness than the frequency band such as 2.4 GHz band and 5 GHz band, is used.

It should be noted that the frequency band of the radio waves emitted by the antenna 27 is not limited to the 60 GHz band, and may be another frequency band. The frequency bands such as the 2.4 GHz band and the 5 GHz band compliant with the wireless LAN standard may be used. It should be noted that the technology of the present disclosure is highly necessary in a case in which there are the merits described above, as compared with a case in which the radio waves compliant with the wireless LAN standard are used, and the radio waves having the frequency than the radio waves compliant with the wireless LAN standard is used.

In addition, in the present example, the arm 23 of the radiography apparatus 11 is the C-arm. The radiography apparatus 11 having the C-arm is often used for the motion picture capturing. Since motion picture has a large amount of data and requires continuous communication, it is highly necessary to make the quality of wireless communication more stable. Therefore, the technology of the present disclosure is particularly effective for the radiography apparatus 11 having the C-arm.

In addition, in the present example, the antenna 27 is provided on the upper surface 24A side of the body part 24. The number of shields that block the radio waves on the upper portion side is smaller than the number of shields on the lower portion side of the body part 24. Therefore, by disposing the antenna 27 on the upper surface 24A side of the body part 24, blocking of the radio waves is suppressed, so that the communication quality of wireless communication is more stable.

In addition, in the present example, the antenna 27 is provided on the support part 29 that rotatably supports the arm 23, and the support part 29 is disposed on the upper portion side of the body part 24 and can be raised and lowered with respect to the body part 24. Therefore, the antenna 27 is also raised and lowered as the arm 23 is raised and lowered, but the relative height of the antenna 27 to the arm 23 is not changed, so that the radio waves of the antenna 27 are not blocked by the arm 23 due to the change in the height of the arm 23.

In addition, in the present example, the inclined angle $\alpha$ is set to 45°, but $\alpha$ may satisfy Conditional Expression (1).

$$0° < \alpha < 90°$$ Conditional Expression (1)

In a case in which the inclined angle $\alpha$ is 0°, that is, in a case in which the radiation direction RD is the horizontal direction HL, the radio waves are likely to be blocked by the shield, which is not preferable. As described above, in many cases, the number of shields around the radiography apparatus 11 is larger as the distance to the floor surface 30 is shorter. In a case in which the inclined angle α is larger than 0°, the radiation direction RD of the radio waves faces upward, so that the radio waves can be emitted to the upper side on which the number of shields is small. In addition, in a case in which the inclined angle α is 90°, that is, in a case in which the radiation direction RD is the vertical direction, the radio waves emitted from the antenna 27 and reflected by the ceiling 56 are returned to the antenna 27, which is not preferable. Therefore, it is preferable that the inclined angle α satisfy Conditional Expression (1).

Further, it is more preferable that the inclined angle α satisfy Conditional Expression (2).

$$30° < α < 60°$$ Conditional Expression (2)

In a case in which the inclined angle α is 30° or more, it is easy to avoid many of the shields present in a lateral direction of the radiography apparatus 11 as compared with a case in which the inclined angle α is less than 30°. In addition, in a case in which the inclined angle α is 60° or less, it is easy to extend a reach distance of the radio waves in the horizontal direction HL as compared with a case in which the inclined angle α exceeds 60°.

In addition, the inclined angle α of 45° described above is an example of the angle at which the radio waves are not blocked by the arm 23. By setting such an inclined angle α, it is possible to make the communication quality stable. It should be noted that, in the present example, the angle at which the radio waves are not blocked by the arm 23 is set to 45°, but it may be an angle other than 45°. The angle at which the radio waves are not blocked by the arm 23 is appropriately set according to the size of the arm 23, the height of the antenna 27, the distance between the arm 23 and the antenna 27, and the like.

In addition, in the present example, the antenna 27 is attached to the antenna support column 38 extending above the body part 24 from the upper surface 24A side of the body part 24. As a result, the antenna 27 can be disposed at a position higher than the upper surface 24A of the body part 24 as compared with a case in which the antenna support column 38 is not provided. The shield of the radio waves present around the radiography apparatus 11 can be avoided as the position of the antenna 27 is higher, so that the communication quality of wireless communication is more stable.

In addition, in the present example, as shown in FIG. 2, the height T1 of the upper end of the antenna 27 is lower than the highest reachable position T0 at which one end of the arm 23 is reachable. In a case in which the height T1 of the upper end of the antenna 27 is lower than the highest reachable position T0 of the arm 23, there is little concern that the antenna 27 physically interferes with the ceiling 56 and a shadowless lamp installed on the ceiling 56.

In addition, as shown in FIG. 7, the antenna 27 can be rotated around the axis extending in the vertical direction, which is the up-down direction. As a result, even in a case in which the radiography apparatus 11 is moved in the horizontal direction HL due to the traveling of the carriage or the like, the antenna 27 is rotated around the axis extending in the up-down direction, so that it is easy to handle the change in the relative position between the antenna 27 and the monitor apparatus 12, as shown in FIGS. 12 and 13.

In addition, as the reference position shown in (A) of FIG. 7, in a case in which a position at which the arm 23 is present in the radiation direction RD of the radio waves of the antenna 27 is defined as a reference position, a rotation angle range of the antenna 27 is within a range of ±90° with respect to the reference position. In this way, by restricting a part of the rotation angle range, it is possible to handle the change in the relative position between the antenna 27 and the external apparatus such as the monitor apparatus 12 while avoiding physical interference with other parts.

In addition, the radiography apparatus 11 further comprises the console monitor 37 used for the operation, and the antenna 27 can be displaced within a range that does not physically interfere with the console monitor 37. More specifically, as shown in FIG. 7, at least in a state in which the console monitor 37 is at the initial position, the antenna 27 can be displaced within a range that does not physically interfere with the console monitor 37. As a result, it is possible to secure the degree of freedom of the change in the orientation of the antenna 27 as compared with a case in which the console monitor 37 and the antenna 27 physically interfere with each other.

In addition, as shown in FIG. 8, the radiography apparatus 11 of the present example comprises the lock mechanism 41 that fixes the orientation of the antenna 27, so that it is possible to prevent the orientation of the antenna 27 from being inadvertently changed.

In addition, as shown in FIG. 11, the radiography apparatus 11 of the present example comprises the wired output I/F 62 which is an example of the wired communication device using the connection cable 65, in addition to the wireless output I/F 61, which is an example of the wireless communication device using the antenna 27. As a result, even in a case in which wireless communication cannot be used due to the radio wave interference with other devices or a failure of the wireless output I/F 61, it is possible to communicate with the external apparatus such as the monitor apparatus 12 by wired communication.

In addition, the wireless output I/F 61 is the wireless communication device of the wireless HDMI (registered trademark) standard using the radio waves having the frequency band of the 60 GHz band. By using a general-purpose interface, it is possible to reduce the manufacturing cost in addition to increasing the types of external apparatuses that can be connected.

The external apparatus is the monitor apparatus 12 that includes the carriage 54 and can be moved by traveling of the carriage 54. Since both the radiography apparatus 11 and the monitor apparatus 12 are mobile types, the relative position therebetween is likely to be changed. Therefore, the technology of the present disclosure that achieves the stabilization of wireless communication by making the radiation direction RD of the radio waves of the antenna 27 variable is particularly effective for a mobile apparatus.

In addition, in the present example, the antenna 52 can be displaced with respect to the monitor support column 53. Even in a case in which the relative position of the radiography apparatus 11 to the monitor apparatus 12 is changed, a reception state of the radio waves can be improved by the displacement of the antenna 52. As a result, the communication quality can be made more stable.

In addition, in the present example, the antenna 52 is disposed above the monitor 51. Therefore, it is possible to suppress blocking of the radio waves received by the antenna 52 by the monitor 51.

In addition, the monitor apparatus 12 comprises the switcher 68 is disposed on the connection path connecting the monitor 51 and the antenna 52, and selectively outputs, to the monitor 51, the video signal input from the antenna and the video signal input from the wired output I/F 62 of the radiography apparatus 11. By providing the switcher 68, switching to the wired communication in a case in which the wireless communication by the antenna 52 is impossible or failed is easy. This switching may be performed by the manual operation. It should be noted that it is more preferable that the input source of the video signal be automatically switched by the switcher 68. As a result, for example, the operator OP can restart the display of the radiation image on the monitor apparatus 12 by wired communication only by connecting the connection cable 65.

In addition, the radiography apparatus 11 comprises the video splitter 64 that outputs the video signal to be transmitted to the monitor apparatus 12 to both the wired output I/F 62 which is an example of the wired communication device and the wireless output I/F 61 which is an example of the wireless communication device. Therefore, in the radiography apparatus 11, the switcher, as the output destination of the video signal from the controller 63, which switches between the wired output I/F 62 and the wireless output I/F 61 is unnecessary.

It should be noted that, in the present example, the inclined angle α of the antenna 27 is set to 45°. As described above, the inclined angle α of 45° described above is an example of the angle at which the radio waves are not blocked by the arm 23. However, for example, in a case in which the size of the arm 23 is larger and the height of the antenna 27 is lower than that of the present example, even at the inclined angle α of 45°, the arm 23 may also enter the radiation direction RD at the reference position shown in (A) of FIG. 7. Even in such a case, the arm 23 can be avoided by causing the antenna 27 to be rotated around the axis extending in the up-down direction as shown in FIG. 7. That is, the antenna 27 of the present example can change the radiation direction RD to the position at which the radio waves are not blocked by the arm 23. As a result, it is easy to secure the communication quality of wireless communication. In addition, as an example in which the arm 23 enters the radiation direction RD of the radio waves at the reference position shown in (A) of FIG. 7, a case in which the inclined angle α is close to 0° can be considered. Even in such a case, it is possible to avoid the arm 23 by rotating the antenna 27 as shown in (B) of FIG. 7 or (C) of FIG. 7.

Inclined Angle of Antenna Is Variable

Figure 14:
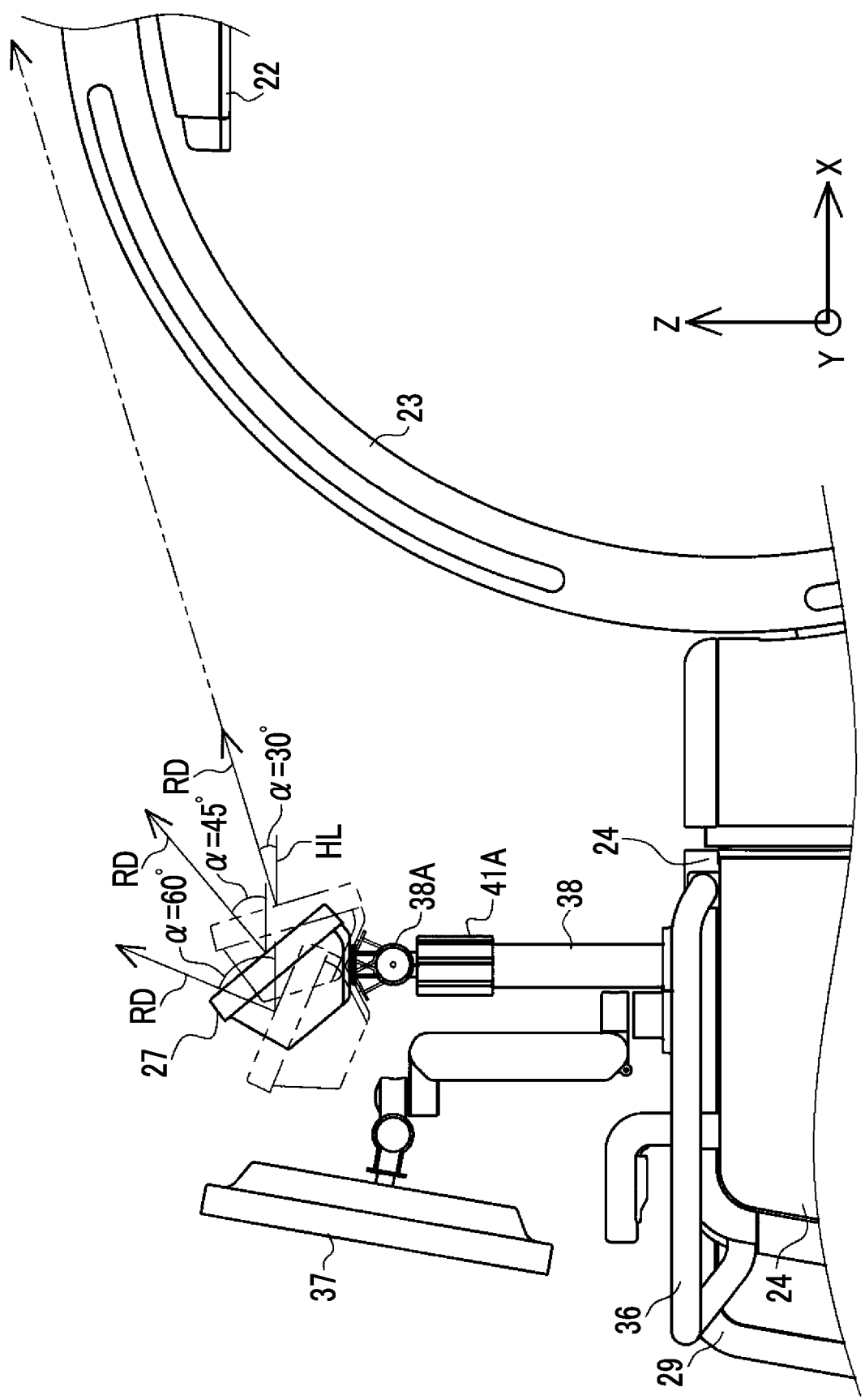
FIG. 14 is a view showing an example of changing an inclined angle of the antenna.

An example shown in FIG. 14 is an example in which the inclined angle α of the antenna 27 is variable. The antenna 27 can be rotated around the axis extending in the Y direction in addition to the rotation around the axis extending in the up-down direction (Z direction in FIG. 14). A rotation mechanism 38A which rotatably supports the antenna 27 is provided at the upper end of the antenna support column 38. The inclined angle α of the antenna 27 is changed by the rotation mechanism 38A in a range of 30° to 60°, for example, with the position at which the inclined angle α is 45° as the reference position. In this way, in a case in which the inclined angle α is variable, an adjustment range of the radiation direction RD of the radio waves is widened, and it is possible to flexibly handle the change in the environment such as the relative positional relationship with the monitor apparatus 12 and the presence or absence of the shield. As a result, it is possible to make the communication quality of wireless communication more stable. It should be noted that, in the present example, the range of the inclined angle α is set to 30° to 60°, but it may be set to a range of 0°<α<90°. In addition, it is preferable that the range of the inclined angle α include the angle at which the radio waves are not blocked by the arm 23.

Antenna Can Be Raised and Lowered

Figure 15:
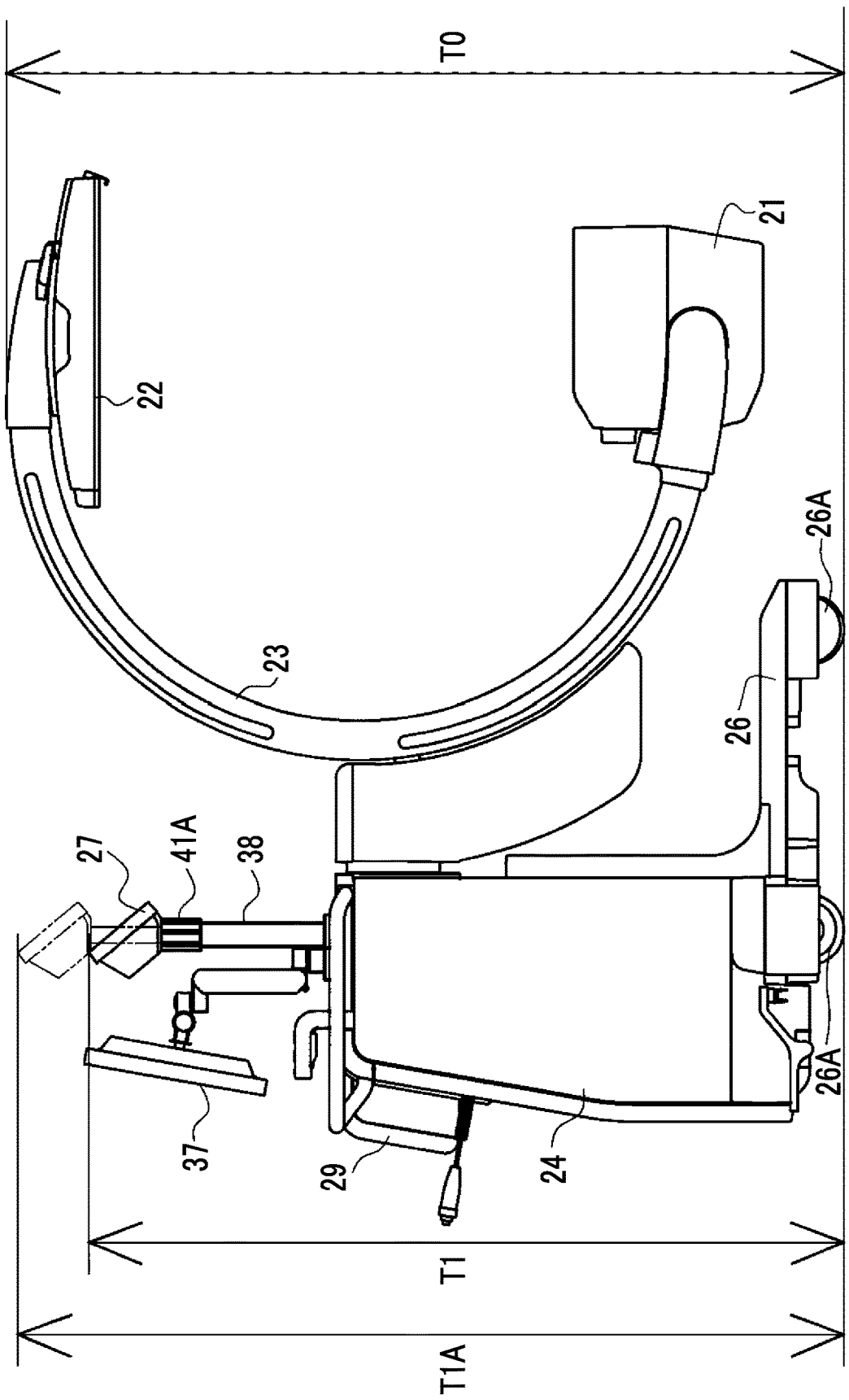
FIG. 15 is a view showing an example of raising and lowering the antenna.

In addition, as shown in FIG. 15, the antenna 27 may be able to be raised and lowered in the up-down direction. As a result, the adjustment range in a height direction of the antenna 27 is widened. Since the antenna 27 can be set at a higher position, it is easy to avoid the shield.

It should be noted that even in a case in which the antenna 27 can be raised and lowered in this way, it is preferable that a highest position T1A of the upper end of the antenna 27 be lower than the highest reachable position T0 of the arm 23. The reason for the above is that it is possible to suppress the physical interference of the antenna 27 with the shadowless lamp or the like installed on the ceiling 56.

Second Embodiment

In the first embodiment, the example has been described in which the orientation of the antenna 27 is manually adjusted, but the radiography apparatus 11 may comprise an orientation adjustment mechanism that adjusts the orientation of the antenna 27 based on the change in the position relative to the external apparatus. As a result, it is easy to adjust the orientation of the antenna 27 according to the change even in a case in which the position relative to the external apparatus is changed.

Orientation Adjustment Mechanism of First Example

Figure 16:
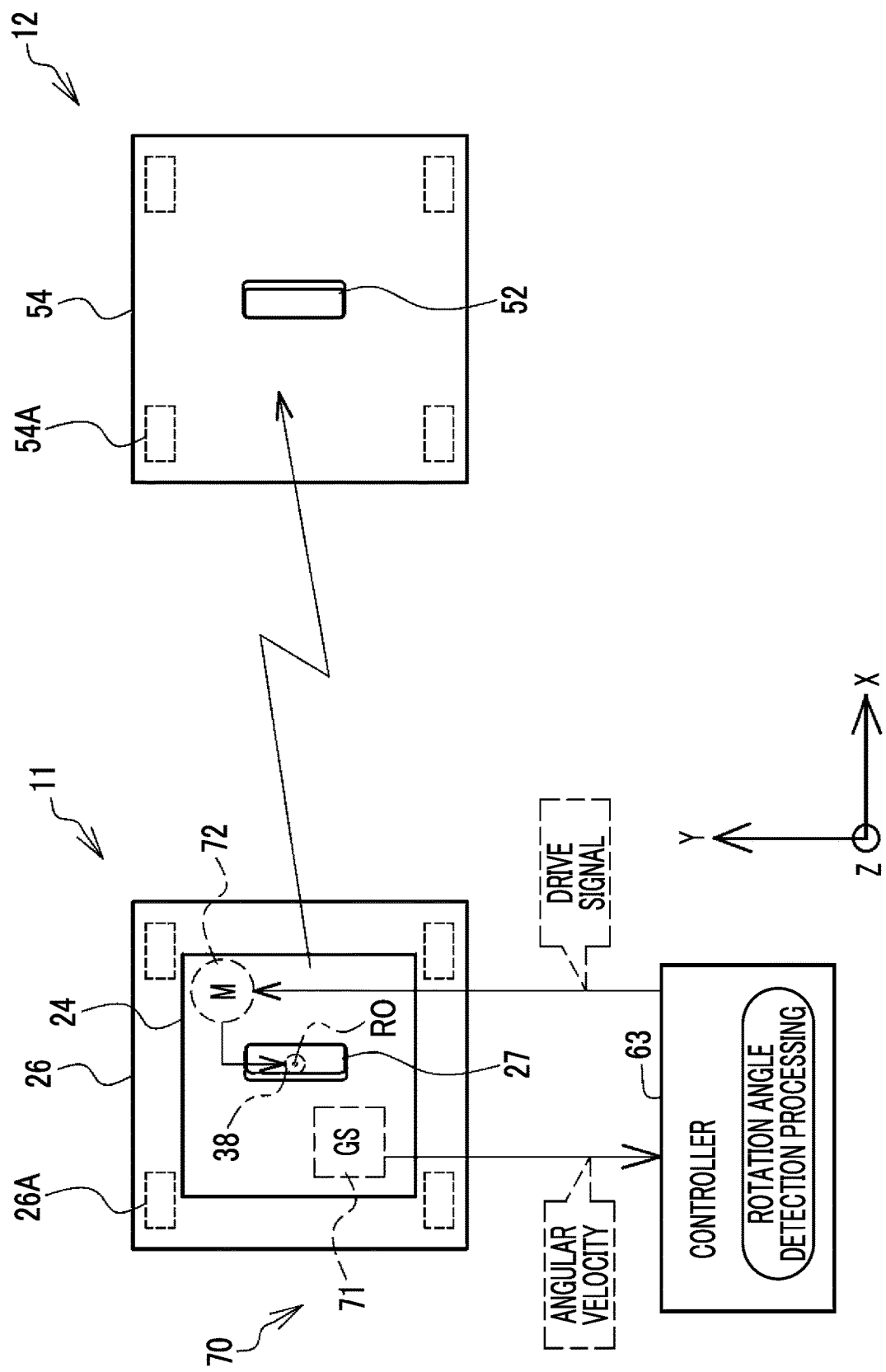
FIG. 16 is a view showing an orientation adjustment mechanism of a first example.
Figure 17:
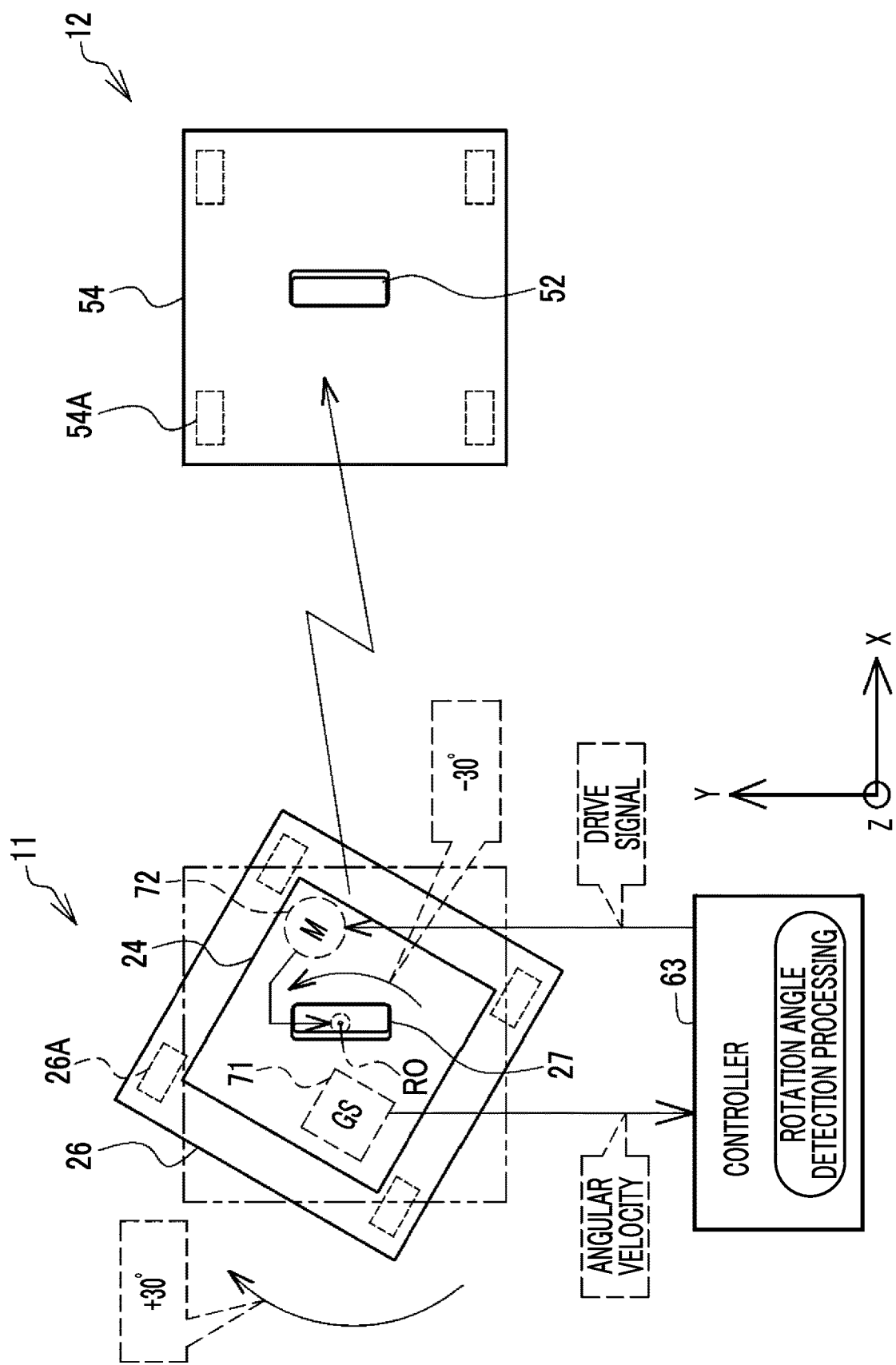
FIG. 17 is an operation view of the orientation adjustment mechanism of the first example.

The radiography apparatus 11 of the example shown in FIGS. 16 and 17 comprises an orientation adjustment mechanism 70. The orientation adjustment mechanism 70 comprises a gyro sensor 71 which is an example of a sensor that detects the rotation of the body part 24 in a case in which the body part 24 is rotated around the axis extending in the up-down direction, which is the vertical direction, and a motor 72 which is an example of an actuator that rotates the antenna 27 in an opposite orientation to the body part 24.

The gyro sensor 71 is provided, for example, on the body part 24, and detects the rotation of the body part 24 in the up-down direction (Z direction in FIG. 16) around the axis. Specifically, the gyro sensor 71 outputs an angular velocity in a case in which the body part 24 is rotated to the controller 63. The controller 63 detects a rotation angle and a rotation direction of the body part 24 based on the input angular velocity. The controller 63 outputs a drive signal for rotating the antenna 27 in the opposite orientation to the motor 72 based on the detected rotation angle and rotation direction. The motor 72 rotates the antenna 27 based on the input drive signal.

For example, as shown in FIG. 16, from a state in which the antenna 27 of the radiography apparatus 11 and the antenna 52 of the monitor apparatus 12 face each other, a case is considered in which the body part 24 is rotated clockwise by +30° as shown in FIG. 17. In this case, the controller 63 outputs the drive signal for rotating the antenna 27 counterclockwise by −30° to the motor 72. As a result, even in a case in which the body part 24 is rotated, since the change in the orientation of the antenna 27 is canceled, the positional relationship in which the antenna 27 of the radiography apparatus 11 and the antenna 52 of the monitor apparatus 12 face each other is maintained.

With such an orientation adjustment mechanism 70, the orientation of the antenna 27 can be made stable regardless of the rotation of the body part 24. As a result, stable communication quality of wireless communication can be maintained even in a case in which the body part 24 is rotated.

Orientation Adjustment Mechanism of Second Example

Figure 18:
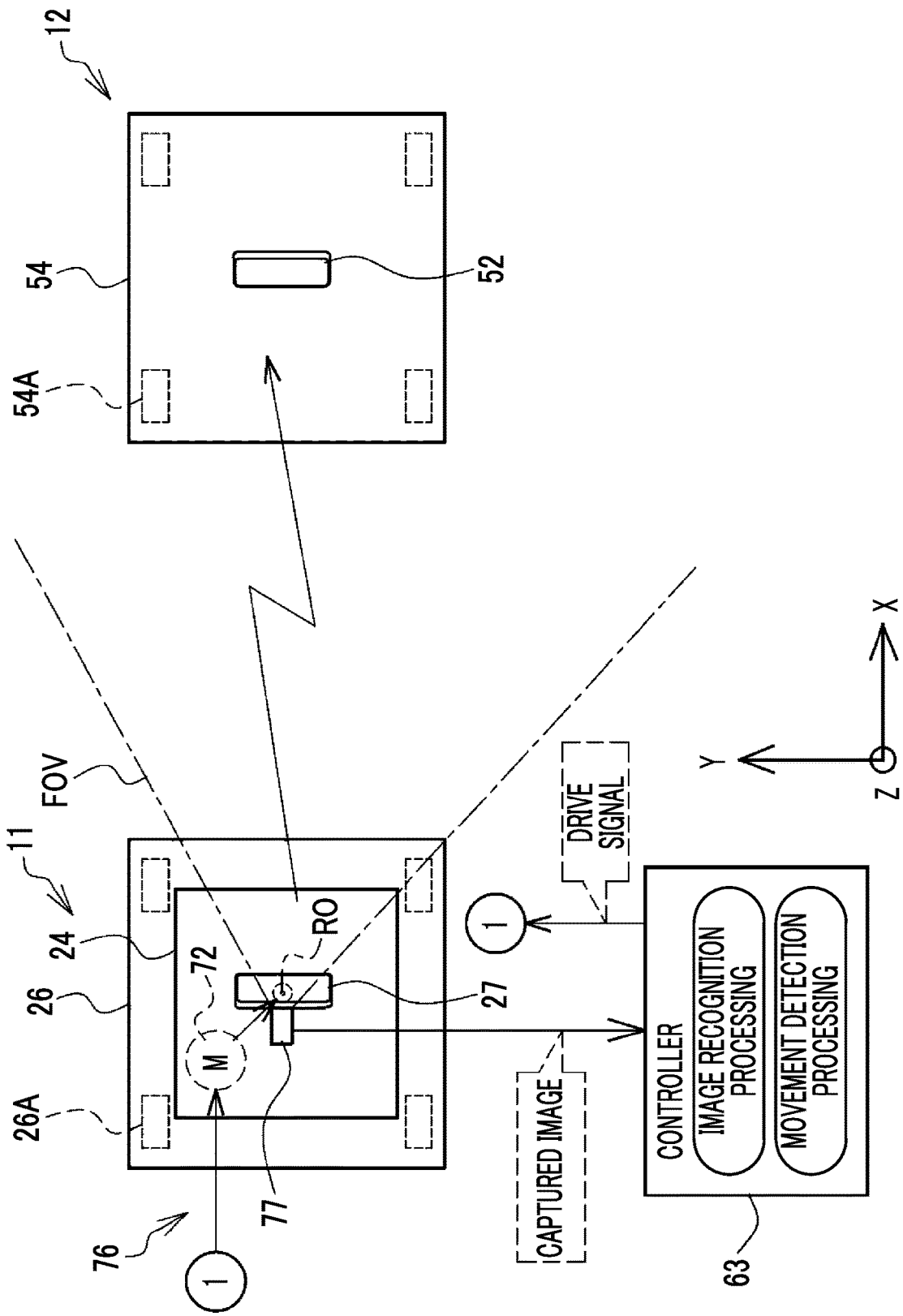
FIG. 18 is a view showing an orientation adjustment mechanism of a second example.
Figure 19:
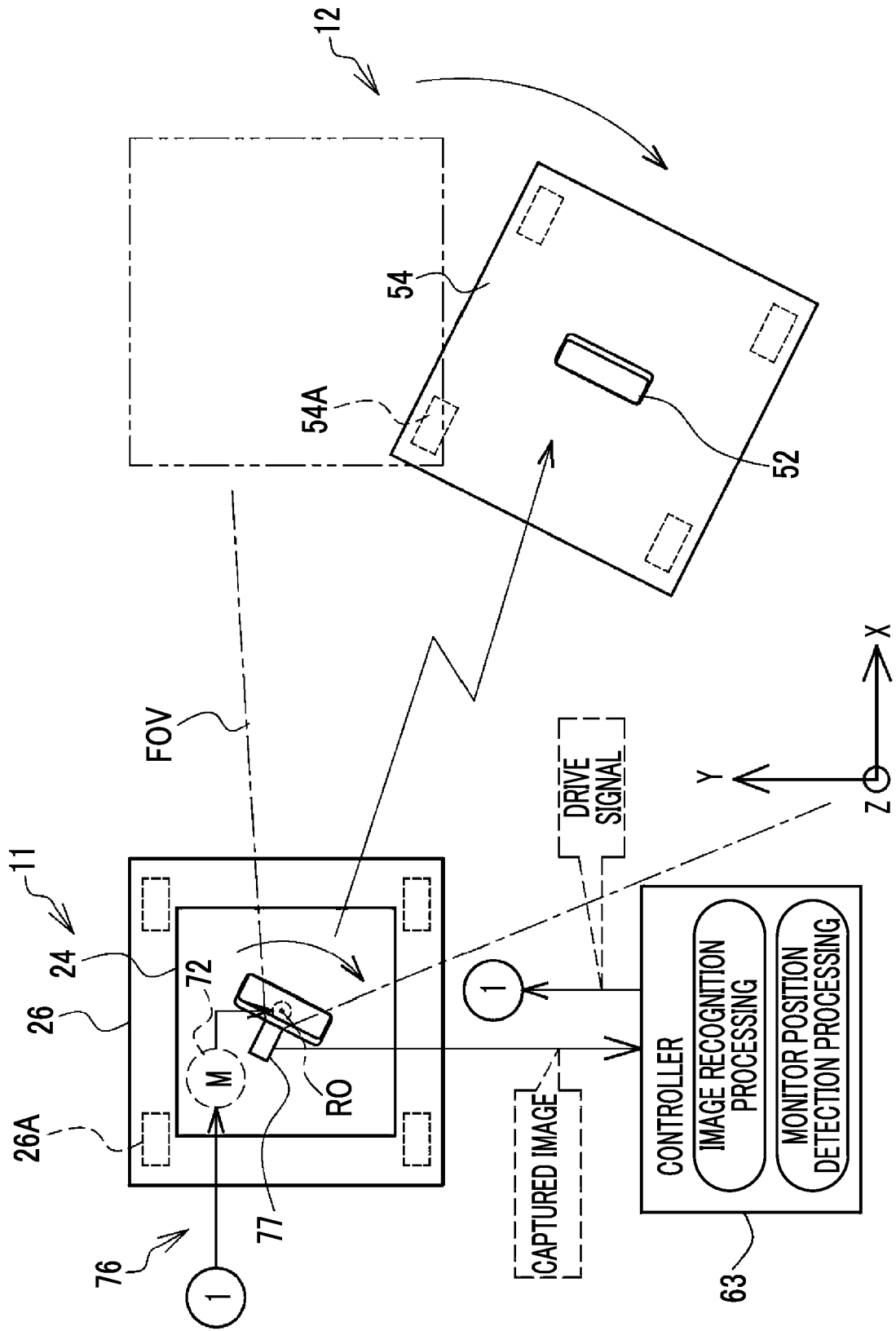
FIG. 19 is an operation view of the orientation adjustment mechanism of the second example.

The radiography apparatus 11 shown in FIGS. 18 and 19 comprises an orientation adjustment mechanism 76 of the second example. The orientation adjustment mechanism 76 comprises a camera 77 which is an example of a position sensor that detects the position of the monitor apparatus 12 as the external apparatus, and the motor 72 which is an example of an actuator that causes the orientation of the antenna 27 to follow the position of the monitor apparatus 12 detected by the camera 77.

The camera 77 is, for example, a digital camera that images the subject based on the visible light. The camera 77 is provided, for example, on the upper portion of the antenna 27, and its posture is adjusted such that the subject present in the radiation direction RD of the antenna 27 is included in a field of view FOV. During activation, the camera 77 captures the motion picture at a preset frame rate, and outputs the captured motion picture to the controller 63 as a captured image.

Therefore, as shown in FIG. 18, in a case in which the monitor apparatus 12 is present at a position facing the antenna 27, the monitor apparatus 12 appears in the captured image output by the camera 77. The controller 63 recognizes the monitor apparatus 12 from the captured images by executing image recognition processing based on the captured image input from the camera 77. The recognition processing of the monitor apparatus 12 is performed by, for example, pattern matching or a method using a machine learning model.

Moreover, the controller 63 executes movement detection processing of detecting a movement direction and a movement amount of the monitor apparatus 12 recognized in the captured image. The controller 63 detects the movement direction of the monitor apparatus 12 that is moved in the captured image. Based on the detected movement direction, the controller 63 changes the orientation of the antenna 27 via the motor 72 such that the monitor apparatus 12 appears at the substantially center of the captured image, for example.

For example, as shown in FIG. 18, in a case in which the monitor apparatus 12 is present at a position facing the antenna 27, the monitor apparatus 12 appears at the substantially center of the captured image of the camera 77. Moreover, a case is considered in which the monitor apparatus 12 is moved from the position shown in FIG. 18 to the position shown in FIG. 19. In this case, the controller 63 detects that the movement direction of the monitor apparatus 12 is the right direction based on the captured image input from the camera 77. Moreover, the controller 63 rotates the antenna 27 clockwise via the motor 72 such that the monitor apparatus 12 appears at the substantially center of the captured image. As a result, the orientation of the antenna 27 follows the position of the monitor apparatus 12.

In this way, the orientation adjustment mechanism 76 comprises the camera 77 as the position sensor that detects the position of the monitor apparatus 12, and the motor 72 that causes the orientation of the antenna 27 to follow the position of the monitor apparatus 12 detected by the camera 77. As a result, wireless communication can be made stable even in a case in which the relative positional relationship between the radiography apparatus 11 and the monitor apparatus 12 as the external apparatus is changed.

Orientation Adjustment Mechanism of Third Example

Figure 20:
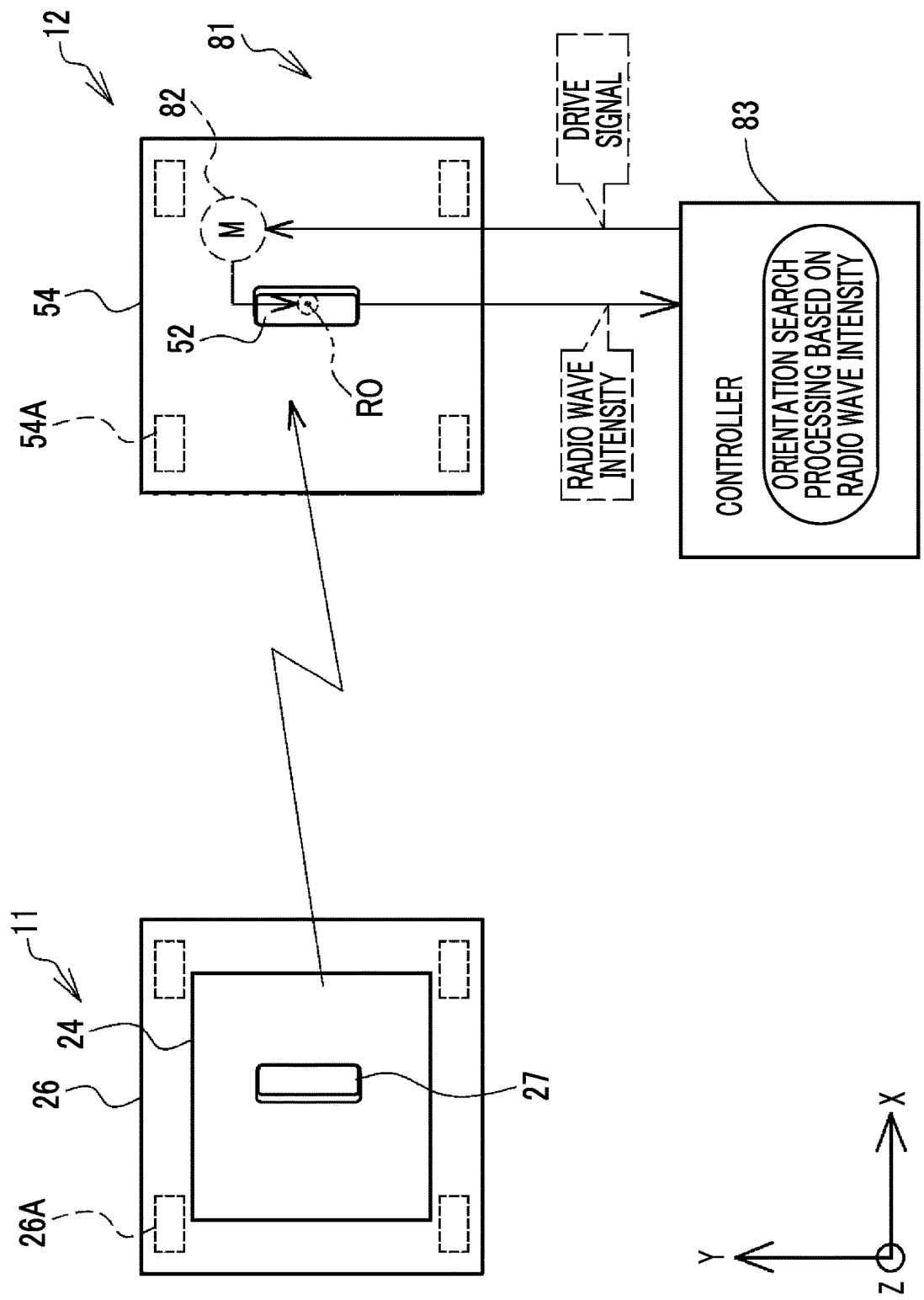
FIG. 20 is a view showing an orientation adjustment mechanism of a third example.
Figure 21:
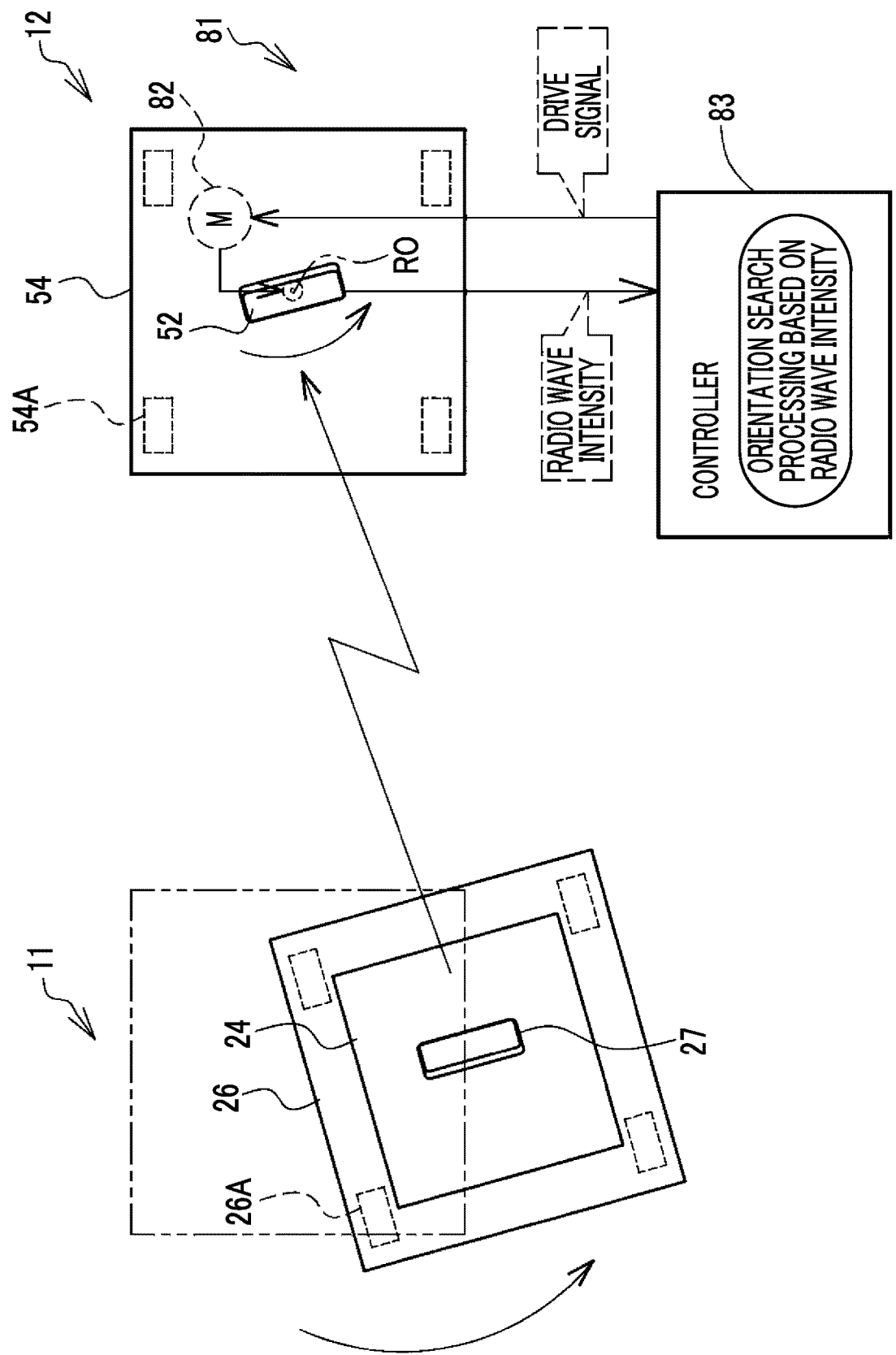
FIG. 21 is an operation view of the orientation adjustment mechanism of the third example.

An orientation adjustment mechanism 81 of the third example shown in FIGS. 20 and 21 is a mechanism that adjusts the orientation of the antenna 52 on the monitor apparatus 12 side which receives the radio waves. The orientation adjustment mechanism 81 has a radio wave intensity detector that detects the radio wave intensity received by the antenna 52, and changes the orientation of the antenna 52 based on the detected radio wave intensity. A controller 83 provided in the monitor apparatus 12 functions as the radio wave intensity detector.

Here, the antenna 27 is an example of a first antenna, the antenna 52 is an example of a second antenna, and the radio wave intensity received by the antenna 52 is an example of the radio wave intensity between the first antenna and the second antenna.

As shown in FIG. 20, the controller 83 acquires the radio wave intensity from the antenna 52. Moreover, the controller 83 executes orientation search processing of searching for an optimum orientation of the antenna 52 based on the radio wave intensity. For example, the controller 83 searches for the orientation in which the radio wave intensity is maximized while rotating the orientation of the antenna 52 via the motor 82. Moreover, the orientation of the antenna 52 is adjusted to the orientation in which the radio wave intensity is maximized.

As shown in FIG. 20, in a state in which the antenna 52 of the monitor apparatus 12 faces the antenna 27 of the radiography apparatus 11, the radio wave intensity of the antenna 52 is maximized. In a case in which the radiography apparatus 11 is moved from a state shown in FIG. 20 as shown in FIG. 21, the radio wave intensity of the antenna 52 is decreased. In this case, the controller 83 searches for the orientation in which the radio wave intensity is maximized while rotating the orientation of the antenna 52, and adjusts the orientation of the antenna 52 based on a search result. As a result, wireless communication can be made stable even in a case in which the relative positional relationship between the radiography apparatus 11 and the monitor apparatus 12 as the external apparatus is changed.

In addition, in the present example, the example has been described in which the orientation of the antenna 52 is adjusted based on the radio wave intensity received by the antenna 52 of the monitor apparatus 12, but the orientation of the antenna 27 may be adjusted based on the radio wave intensity received by the antenna 27 of the radiography apparatus 11. In addition, the radio wave intensity of each of the antenna 27 and the antenna 52 may be detected. In addition, the orientations of both the antenna 27 and the antenna 52 may be adjusted.

Third Embodiment

Figure 22:
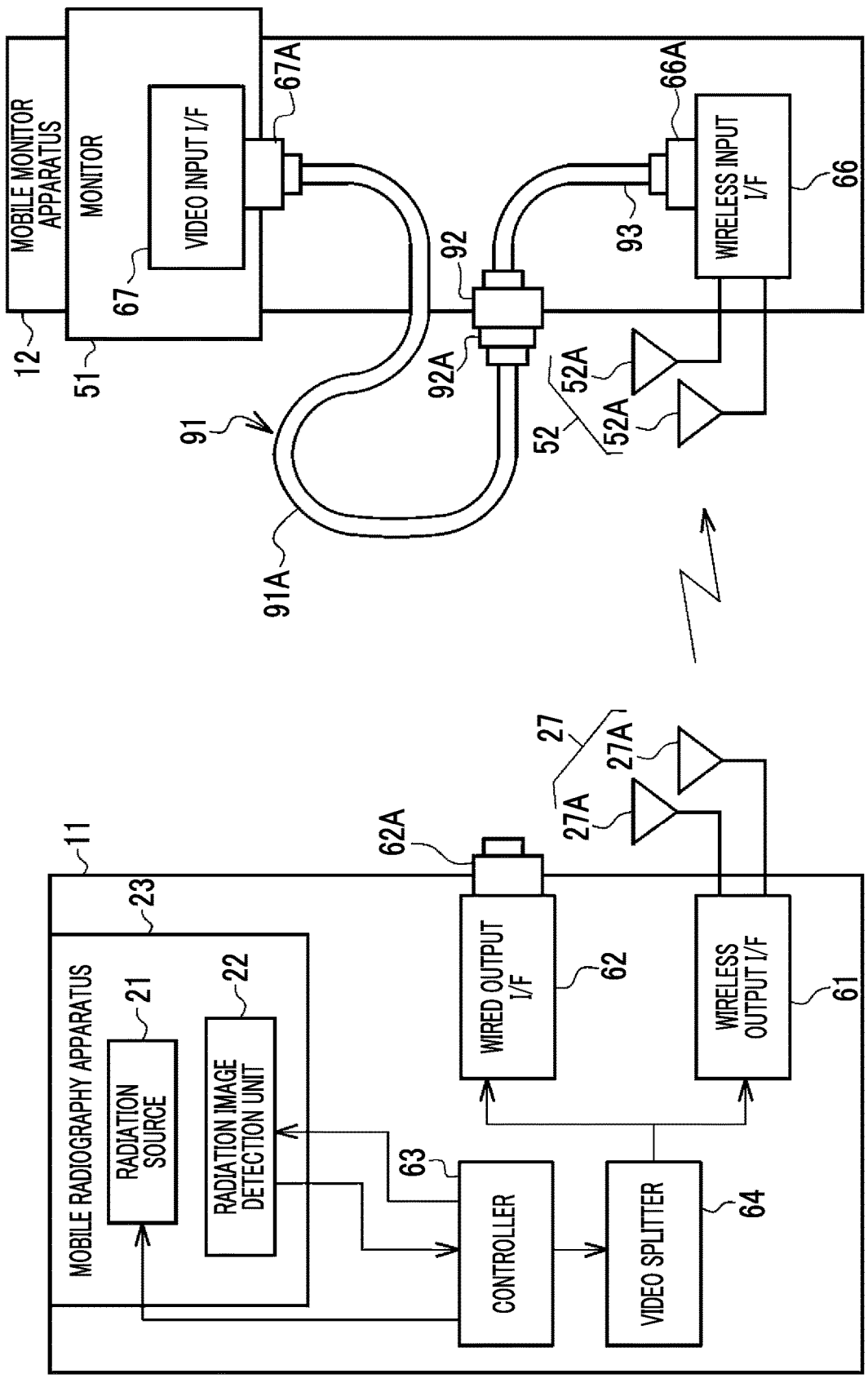
FIG. 22 is a view showing a connection state of a connection cable in a case in which wireless communication is performed.
Figure 23:
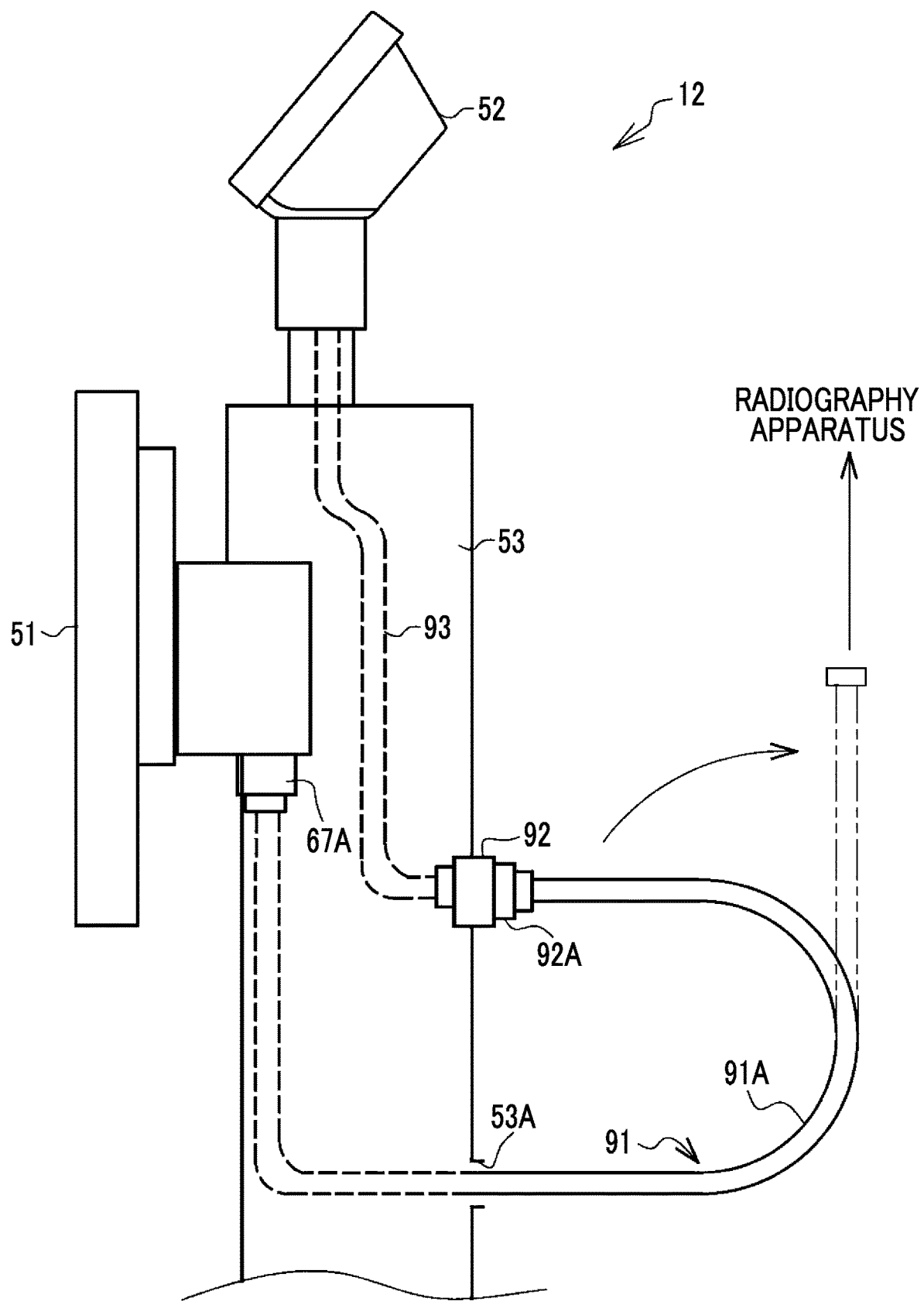
FIG. 23 is a view showing an arrangement of relays.
Figure 24:
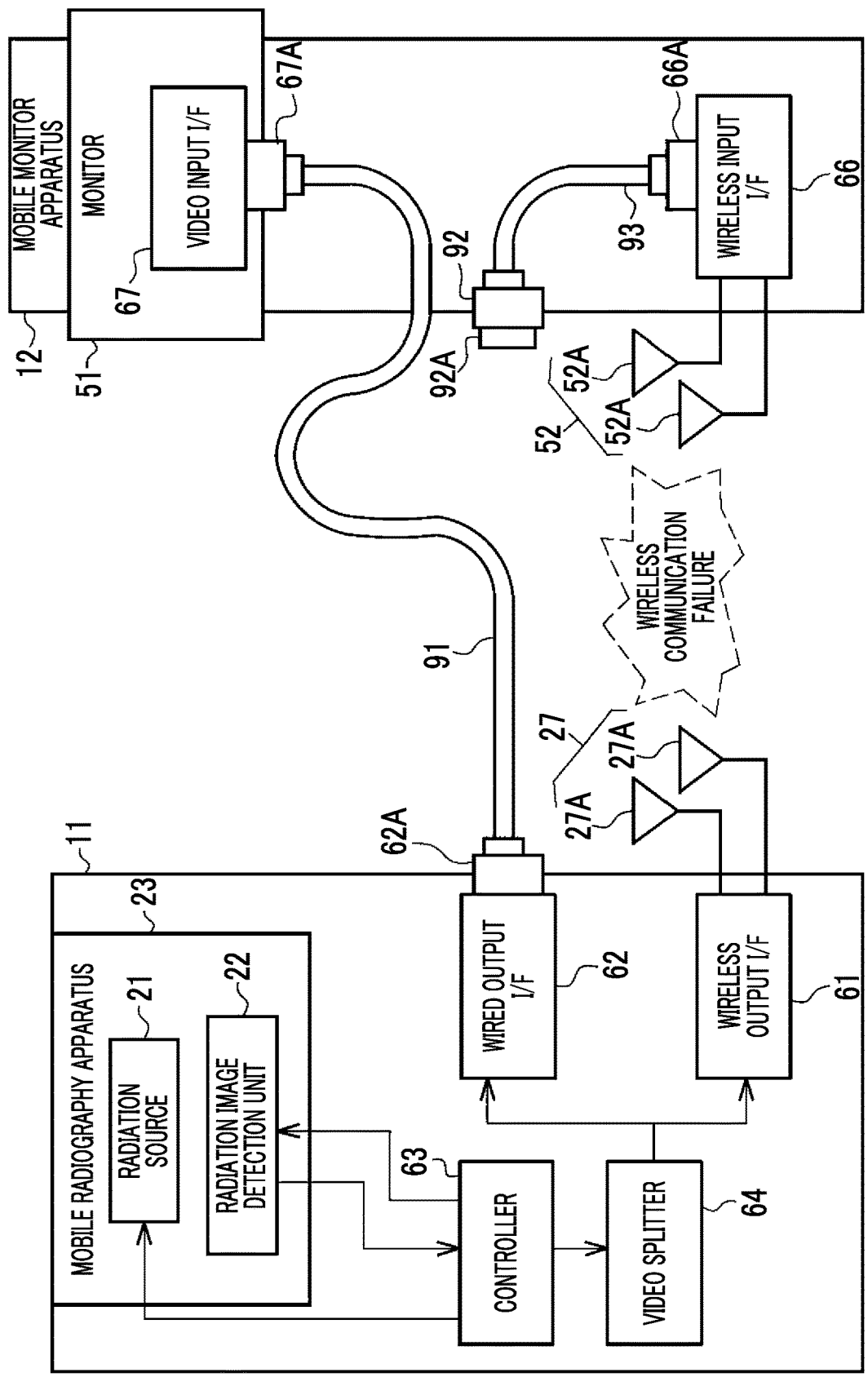
FIG. 24 is a view showing a connection state of a connection cable in a case in which wired communication is performed.

A third embodiment shown in FIGS. 22 to 24 is characterized by a method of switching between wired communication and wireless communication in the monitor apparatus 12. The radiography apparatus 11 has the same configuration as shown in FIG. 11, and the wired output I/F 62 as the wired communication device includes the connector 62A as a first cable connector for connecting a connection cable 91 from the monitor apparatus 12.

On the other hand, the monitor apparatus 12 comprises the connection cable 91 for connecting the monitor 51 and the antenna 52 as the second antenna, and a relay 92 that includes a connector 92A as a second cable connector which is disposed between the antenna 52 and the connection cable 91 and to which one end of the connection cable 91 can be attached and detached. Moreover, one end of the connection cable 91 removed from the connector 92A of the monitor apparatus 12 can be connected to the connector 62A as the first cable connector of the radiography apparatus 11.

The relay 92 is connected to the wireless input I/F 66 by an internal cable 93. The connector 92A of the relay 92 is a connector compliant with the DVI standard similar to the connector 62A and the connector 67A. As shown in FIG. 23, in the monitor apparatus 12, the connector 92A of the relay 92 is provided on the monitor support column 53 and is exposed to the outside.

One end of the connection cable 91 is connected to the connector 67A of the video input I/F 67 of the monitor 51. Moreover, in a case in which wireless communication is performed between the wireless output I/F 61 and the wireless input I/F 66, the other end of the connection cable 91 is connected to the connector 92A of the relay 92. As shown in FIG. 23, for example, the connection cable 91 passes through the inside of the monitor support column 53 from the connector 67A of the monitor 51, and a part thereof including the other end of the connection cable 91 is drawn out from an opening 53A formed on the monitor support column 53 to the outside of the monitor support column 53. Moreover, the other end of the connection cable 91 drawn out from the monitor support column 53 is connected to the connector 92A of the relay 92. In the connection cable 91, a length of a drawer part 91A drawn out from the monitor support column 53 is, for example, several meters. The drawer part 91A is, for example, hooked on a hook (not shown) provided on the monitor support column 53 in a state of being wound and bundled in an annular shape.

Moreover, in a case in which a wireless communication failure occurs as shown in FIG. 24, the operator OP removes the other end of the connection cable 91 connected to the connector 92A from the connector 92A, and extends the drawer part 91A wound in an annular shape to the radiography apparatus 11 to be connected to the connector 62A of the wired output I/F 62. As a result, the wired output I/F 62 of the radiography apparatus 11 and the video input I/F 67 of the monitor apparatus 12 are connected by the connection cable 91, and wired communication is possible.

In this way, according to the present example, since it is possible to switch from wireless communication to wired communication simply by replacing the other end of the connection cable 91 from the connector 92A of the relay 92 to the connector 92A of the wired output I/F 62, the switching operation is very easy. In addition, in the monitor apparatus 12, the connection cable 91 used for wireless communication is also used for wired communication. In addition, one video input I/F 67 provided on the monitor 51 can be used for both wired communication and wireless communication without using the switcher 68 as shown in FIG. 11. Therefore, an apparatus configuration of the monitor apparatus 12 can be simplified.

In each of the embodiments described above, the monitor apparatus 12 has been described as an example of the external apparatus, but the external apparatus may be an apparatus other than the monitor apparatus 12. The external apparatus other than the monitor apparatus 12 may be an image processing apparatus that executes diagnostic support processing by a computer on the radiation image captured by the radiography apparatus 11. As a method of using such an image processing apparatus, for example, the radiation image captured by the radiography apparatus 11 is transmitted to the image processing apparatus, and the processing result processed by the image processing apparatus is returned to the radiography apparatus 11. In such a case, bidirectional communication is required between the radiography apparatus 11 and the external apparatus, so that a wireless communication device that can perform bidirectional communication is provided as the wireless communication device of each of the radiography apparatus 11 and the external apparatus.

Among such image processing apparatuses, in addition to a stationary type such as a server apparatus, a small portable type is developed. By combining the radiography apparatus 11 and the portable type image processing apparatus, rapid image diagnosis is possible.

In addition, in each of the embodiments described above, the C-arm that can be orbitally rotated and can be axially rotated has been described as an example of the arm 23, but the arm 23 may be an arm that can only be axially rotated, for example, a U-arm in which a side surface shape is U-shape.

It should be noted that X-rays have been described as an example of the radiation, but the radiation is not limited to the X-rays, and may be γ-rays or the like.

In each of the embodiments described above, as the hardware structure of the wireless output I/F 61 and the wireless input I/F 66 as examples of the wireless communication device, the wired output I/F 62 as an example of the wired communication device, and the processing unit that executes various pieces of processing, such as the controller 63 and the controller 83, various processors described below can be used. The various processors include, in addition to the CPU which is a general-purpose processor that executes the software and functions as various processing units, a programmable logic device (PLD) which is a processor of which a circuit configuration can be changed after the manufacture, such as a field programmable gate array (FPGA), a dedicated electric circuit which is a processor having a dedicated circuit configuration designed to execute specific processing, such as an application specific integrated circuit (ASIC), and the like.

One processing unit may be configured by one of various processors described above or may be configured by a combination of two or more processors (for example, a combination of a plurality of FPGAs and/or a combination of the CPU and the FPGA) of the same type or different types. In addition, a plurality of processing units may be configured by one processor.

As an example in which a plurality of processing units are configured by one processor, there is a form in which one processor is configured by a combination of one or more CPUs and the software, and the processor functions as a plurality of processing units. Second, as represented by a system on chip (SoC) and the like, there is a form in which a processor is used that realizes the functions of the entire system including a plurality of processing units with a single integrated circuit (IC) chip. In this way, various processing units are configured by one or more of the various processors as the hardware structure.

Further, as the hardware structure of these various processors, more specifically, it is possible to use an electrical circuit (circuitry) in which circuit elements such as semiconductor elements are combined.

The technology of the present disclosure can also be appropriately combined with various embodiments and/or various modification examples described above. In addition, it is needless to say that the technology of the present disclosure is not limited to the embodiments described above, and various configurations can be employed without departing from the gist of the technology of the present disclosure.

The following technology can be grasped by the above description.

Supplementary Note 1

A mobile radiography system comprising a mobile radiography apparatus, and a mobile monitor apparatus, in which the mobile radiography apparatus includes a radiation source, a radiation image detector that detects a radiation image of a subject by receiving radiation emitted from the radiation source and transmitted through the subject, an arm that holds the radiation source and the radiation image detector, a body part to which the arm is rotatably attached, a carriage on which the body part is mounted, and a first antenna that emits a radio wave for wirelessly communicating with an external apparatus, the first antenna being provided in a portion in which a radiation direction of the radio wave is not changed even in a case in which the arm is rotated and capable of changing the radiation direction of the radio wave, and the mobile monitor apparatus includes a monitor, a second antenna that receives the radio wave from the first antenna, a monitor support column that holds the monitor and the second antenna, and a carriage on which the monitor support column is mounted.

Here, an example of the first antenna is the antenna 27, and an example of the second antenna is the antenna 52.

Supplementary Note 2

The mobile radiography system according to Supplementary Note 1, in which the second antenna is displaceable with respect to the monitor support column.

Supplementary Note 3

The mobile radiography system according to Supplementary Note 1 or 2, in which the second antenna is disposed above the monitor.

Supplementary Note 4

The mobile radiography system according to any one of Supplementary Notes 1 to 3, further comprising an orientation adjustment mechanism that adjusts an orientation of the antenna based on a change in a relative position between the mobile radiography apparatus and the mobile monitor apparatus.

Supplementary Note 5

The mobile radiography system according to Supplementary Note 4, further comprising a radio wave intensity detector that detects a radio wave intensity between the first antenna and the second antenna, and an orientation adjustment mechanism that changes an orientation of at least one of the first antenna or the second antenna based on the detected radio wave intensity.

Supplementary Note 6

The mobile radiography system according to Supplementary Note 4, in which the orientation adjustment mechanism includes a position sensor that detects a position of the mobile monitor apparatus or the mobile radiography apparatus, and an actuator that causes the orientation of the first antenna or the second antenna to follow the position of the mobile monitor apparatus or the mobile radiography apparatus detected by the position sensor.

Supplementary Note 7

The mobile radiography system according to any one of Supplementary Notes 1 to 6, in which each of the mobile radiography apparatus and the mobile monitor apparatus includes a wired communication device that performs wired communication using a cable in addition to a wireless communication device that performs wireless communication using the first antenna and the second antenna.

Supplementary Note 8

The mobile radiography system according to Supplementary Note 7, in which, in the mobile radiography apparatus, the wired communication device includes a first cable connector for connecting a connection cable from the mobile monitor apparatus, the mobile monitor apparatus includes a connection cable that connects the monitor and the second antenna, and a second cable connector which is disposed between the second antenna and the connection cable, and to which one end of the connection cable is attachable and detachable, and the one end of the connection cable removed from the second cable connector of the mobile monitor apparatus is connectable to the first cable connector of the mobile radiography apparatus.

Supplementary Note 9

The mobile radiography system according to Supplementary Note 8, in which the mobile monitor apparatus includes a switcher that is disposed on a connection path connecting the monitor and the second antenna, and selectively outputs, to the monitor, a video signal input from the second antenna and a video signal input from the wired communication device of the mobile radiography apparatus.

Supplementary Note 10

The mobile radiography system according to any one of Supplementary Notes 7 to 9, in which the mobile radiography apparatus includes a video splitter that outputs a video signal to be transmitted to the mobile monitor apparatus to both the wired communication device and the wireless communication device.

The contents described and shown above are the detailed description of the parts relating to the technology of the present disclosure, and are merely an example of the technology of the present disclosure. For example, the above description of the configuration, the function, the action, and the effect are the description of examples of the configuration, the function, the action, and the effect of the parts relating to the technology of the present disclosure. Therefore, it is needless to say that unnecessary parts may be deleted, new elements may be added, or replacements may be made with respect to the contents described and shown above within a range that does not deviate from the gist of the technology of the present disclosure. In addition, in order to avoid complications and facilitate understanding of the parts relating to the technology of the present disclosure, in the contents described and shown above, the description of common general knowledge and the like that do not particularly require description for enabling the implementation of the technology of the present disclosure are omitted.

In the present specification, "A and/or B" is synonymous with "at least one of A or B". That is, "A and/or B" means that it may be only A, only B, or a combination of A and B. In addition, in the present specification, in a case in which three or more matters are associated and expressed by "and/or", the same concept as "A and/or B" is applied.

All documents, patent applications, and technical standards described in the present specification are incorporated in the present specification by reference to the same extent as in a case in which each document, each patent application, and each technical standard are specifically and individually described by being incorporated by reference.

What is claimed is:

1. A mobile radiography apparatus comprising:
   a radiation source;
   a radiation image detector that detects a radiation image of a subject by receiving radiation emitted from the radiation source and transmitted through the subject;
   an arm that holds the radiation source and the radiation image detector;
   a body part to which the arm is rotatably attached;
   a carriage on which the body part is mounted; and
   an antenna that emits a radio wave for wirelessly communicating with an external apparatus, the antenna being provided in a portion in which a radiation direction of the radio wave is not changed even in a case in which the arm is rotated and capable of changing the radiation direction of the radio wave,
   wherein the antenna is rotatable around an axis extending in a vertical direction, and
   wherein, in a case in which a position at which the arm is present in the radiation direction of the radio wave of the antenna is defined as a reference position, a rotation angle range of the antenna is within a range of ±90° with respect to the reference position.

2. The mobile radiography apparatus according to claim 1,
   wherein a frequency band of the radio wave is a 60 GHz band.

3. The mobile radiography apparatus according to claim 1,
   wherein the arm is a C-arm having a C-shape as viewed in a side view.

4. The mobile radiography apparatus according to claim 1,
   wherein the antenna is provided on an upper surface side of the body part.

5. The mobile radiography apparatus according to claim 4, further comprising:
   a support part that rotatably supports the arm, the support part being disposed on an upper portion side of the body part and capable of being raised and lowered with respect to the body part,
   wherein the antenna is provided on the support part.

6. The mobile radiography apparatus according to claim 1,
   wherein the radiation direction in which the antenna emits the radio wave is inclined upward with respect to a horizontal direction, and
   in a case in which an inclined angle with respect to the horizontal direction is defined as α, α satisfies Conditional Expression (1), $$0° < \alpha < 90°$$ Conditional Expression (1).

7. The mobile radiography apparatus according to claim 6,
   wherein the inclined angle is fixed at an angle at which the radio wave is not blocked by the arm.

8. The mobile radiography apparatus according to claim 6,
   wherein the inclined angle of the antenna is variable.

9. The mobile radiography apparatus according to claim 1,
   wherein the antenna is attached to an antenna support column extending from an upper surface side of the body part to an upper side of the body part.

10. The mobile radiography apparatus according to claim 1,
    wherein an upper end of the antenna is lower than a highest reachable position at which one end of the arm is reachable.

11. The mobile radiography apparatus according to claim 1, further comprising:
    a console monitor used for an operation,
    wherein the antenna is displaceable within a range that does not physically interfere with the console monitor.

12. The mobile radiography apparatus according to claim 1, further comprising:
    a lock mechanism that fixes an orientation of the antenna.

13. The mobile radiography apparatus according to claim 1, further comprising:
    a wired communication device that uses a cable in addition to a wireless communication device that uses the antenna.

14. The mobile radiography apparatus according to claim 1,
    wherein a wireless communication device that performs wireless communication using the antenna is a wireless communication device of a wireless HDMI (registered trademark) standard that uses a radio wave having a frequency band of a 60 GHz band.

15. A mobile radiography apparatus comprising:
    a radiation source;
    a radiation image detector that detects a radiation image of a subject by receiving radiation emitted from the radiation source and transmitted through the subject;
    an arm that holds the radiation source and the radiation image detector;
    a body part to which the arm is rotatably attached;
    a carriage on which the body part is mounted;
    an antenna that emits a radio wave for wirelessly communicating with an external apparatus, the antenna being provided in a portion in which a radiation direction of the radio wave is not changed even in a case in which the arm is rotated and capable of changing the radiation direction of the radio wave; and
    an orientation adjustment mechanism that adjusts an orientation of the antenna based on a change in a position relative to the external apparatus.

16. The mobile radiography apparatus according to claim 15,
    wherein the orientation adjustment mechanism includes
    a sensor that detects a rotation of the body part around an axis extending in a vertical direction, and
    an actuator that rotates the antenna in an opposite orientation to the body part.

17. The mobile radiography apparatus according to claim 15,
    wherein the orientation adjustment mechanism includes
    a position sensor that detects a position of the external apparatus, and an actuator that causes the orientation of the antenna to follow the position of the external apparatus detected by the position sensor.

18. A mobile radiography apparatus comprising:

a radiation source;

a radiation image detector that detects a radiation image of a subject by receiving radiation emitted from the radiation source and transmitted through the subject;

an arm that holds the radiation source and the radiation image detector;

a body part to which the arm is rotatably attached;

a carriage on which the body part is mounted; and an antenna that emits a radio wave for wirelessly communicating with an external apparatus, the antenna being provided in a portion in which a radiation direction of the radio wave is not changed even in a case in which the arm is rotated and capable of changing the radiation direction of the radio wave, wherein the external apparatus is a mobile monitor apparatus that includes a carriage and is movable by traveling of the carriage.

\* \* \* \* \*